US007893028B2

(12) United States Patent
Imamura et al.

(10) Patent No.: US 7,893,028 B2
(45) Date of Patent: Feb. 22, 2011

(54) ISOLATED MUTANT PROTEIN OF FIBROBLAST GROWTH FACTOR 18 AND PHARMACEUTICAL COMPOSITION COMPRISING THE SAME

(75) Inventors: Toru Imamura, Tsukuba (JP); Nozomi Tsujino, Tsukuba (JP); Masashi Suzuki, Tsukuba (JP); Masahiro Asada, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 49 days.

(21) Appl. No.: 12/159,854

(22) PCT Filed: Jan. 9, 2007

(86) PCT No.: PCT/JP2007/050070

§ 371 (c)(1),
(2), (4) Date: Jul. 1, 2008

(87) PCT Pub. No.: WO2007/080847

PCT Pub. Date: Jul. 19, 2007

(65) Prior Publication Data

US 2009/0286965 A1    Nov. 19, 2009

(30) Foreign Application Priority Data

Jan. 11, 2006   (JP)   ............................. 2006-004210

(51) Int. Cl.
*A61K 38/18*   (2006.01)
*C07K 14/50*   (2006.01)

(52) U.S. Cl. .............................. 514/12; 514/2; 530/399
(58) Field of Classification Search .................. None
See application file for complete search history.

(56) References Cited

FOREIGN PATENT DOCUMENTS

JP    11-332570 A    12/1999

OTHER PUBLICATIONS

International Search report for International application No. PCT/JP2007/050070, Japanese Patent Office, mailed Feb. 6, 2007.
Konishi-Tsujino N., et al., "Biological activity of the amino-terminal deletion mutants of FGF18 protein", (*Signal. mol. res. lab., natl. inst. AIST*) Aug. 25, 2005, vol. 77, No. 8, p. 844, 2P-624.
Obayashi N., et al., FGF18 is required for normal cell proliferation and differentiation during osteogenesis and chondrogenesis., Genes Dev., 2002, vol. 16, No. 7, p. 870-879.
Kawano M., et al., Comprehensive analysis of FGF and FGFR expression in skin: FGF18 is highly expressed in hair follicles and capable of inducing anagen from telogen stage hair follicles., 2005, vol. 124, No. 5, p. 877-885.

*Primary Examiner*—Christine J Saoud
(74) *Attorney, Agent, or Firm*—Hogan Lovells US LLP

(57) ABSTRACT

Disclosed is a mutant protein having an altered fibroblast growth factor receptor specificity, which is produced by deleting one or more amino acid residues from the N-terminus of the amino acid sequence of naturally secreted fibroblast growth factor 18. The protein mutant can be used in a pharmaceutical composition for regulating hair regeneration or growth or a pharmaceutical composition for regulating bone or cartilage formation.

13 Claims, 7 Drawing Sheets

Lane 1: FGF18
Lane 2: Δ4-FGF18
Lane 3: Δ12-FGF18
Lane 4: Δ16-FGF18
Lane 5: Δ18-FGF18
Lane 6: Δ22-FGF18
Lane 7: Δ37-FGF18
Lane 8: Δ48-FGF18
Lane 9: Δ67-FGF18
Lane 10: Δ77-FGF18
Lane 11: Δ95-FGF18

SEQUENCE LISTING

```
<160> NUMBER OF SEQ ID NOS: 71

<210> SEQ ID NO 1
<211> LENGTH: 182
<212> TYPE: PRT
<213> ORGANISM: Homo sapiens

<400> SEQUENCE: 1

Met Ala Glu Glu Asn Val Asp Phe Arg Ile His Val Glu Asn Gln Thr
1               5                   10                  15

Arg Ala Arg Asp Asp Val Ser Arg Lys Gln Leu Arg Leu Tyr Gln Leu
            20                  25                  30

Tyr Ser Arg Thr Ser Gly Lys His Ile Gln Val Leu Gly Arg Arg Ile
        35                  40                  45

Ser Ala Arg Gly Glu Asp Gly Asp Lys Tyr Ala Gln Leu Leu Val Glu
    50                  55                  60

Thr Asp Thr Phe Gly Ser Gln Val Arg Ile Lys Gly Lys Glu Thr Glu
65                  70                  75                  80

Phe Tyr Leu Cys Met Asn Arg Lys Gly Lys Leu Val Gly Lys Pro Asp
                85                  90                  95

Gly Thr Ser Lys Glu Cys Val Phe Ile Glu Lys Val Leu Glu Asn Asn
            100                 105                 110

Tyr Thr Ala Leu Met Ser Ala Lys Tyr Ser Gly Trp Tyr Val Gly Phe
        115                 120                 125

Thr Lys Lys Gly Arg Pro Arg Lys Gly Pro Lys Thr Arg Glu Asn Gln
    130                 135                 140

Gln Asp Val His Phe Met Lys Arg Tyr Pro Lys Gly Gln Pro Glu Leu
145                 150                 155                 160

Gln Lys Pro Phe Lys Tyr Thr Thr Val Thr Lys Arg Ser Arg Arg Ile
                165                 170                 175

Arg Pro Thr His Pro Ala
180

<210> SEQ ID NO 2
<211> LENGTH: 178
<212> TYPE: PRT
<213> ORGANISM: Homo sapiens

<400> SEQUENCE: 2

Met Val Asp Phe Arg Ile His Val Glu Asn Gln Thr Arg Ala Arg Asp
1               5                   10                  15

Asp Val Ser Arg Lys Gln Leu Arg Leu Tyr Gln Leu Tyr Ser Arg Thr
            20                  25                  30

Ser Gly Lys His Ile Gln Val Leu Gly Arg Arg Ile Ser Ala Arg Gly
        35                  40                  45

Glu Asp Gly Asp Lys Tyr Ala Gln Leu Leu Val Glu Thr Asp Thr Phe
    50                  55                  60
```

```
Gly Ser Gln Val Arg Ile Lys Gly Lys Glu Thr Glu Phe Tyr Leu Cys
 65                  70                  75                  80

Met Asn Arg Lys Gly Lys Leu Val Gly Lys Pro Asp Gly Thr Ser Lys
                 85                  90                  95

Glu Cys Val Phe Ile Glu Lys Val Leu Glu Asn Asn Tyr Thr Ala Leu
            100                 105                 110

Met Ser Ala Lys Tyr Ser Gly Trp Tyr Val Gly Phe Thr Lys Lys Gly
        115                 120                 125

Arg Pro Arg Lys Gly Pro Lys Thr Arg Glu Asn Gln Gln Asp Val His
    130                 135                 140

Phe Met Lys Arg Tyr Pro Lys Gly Gln Pro Glu Leu Gln Lys Pro Phe
145                 150                 155                 160

Lys Tyr Thr Thr Val Thr Lys Arg Ser Arg Ile Arg Pro Thr His
                165                 170                 175

Pro Ala
```

<210> SEQ ID NO 3
<211> LENGTH: 170
<212> TYPE: PRT
<213> ORGANISM: Homo sapiens

<400> SEQUENCE: 3

```
Met Asn Gln Thr Arg Ala Arg Asp Asp Val Ser Arg Lys Gln Leu Arg
  1               5                  10                  15

Leu Tyr Gln Leu Tyr Ser Arg Thr Ser Gly Lys His Ile Gln Val Leu
                 20                  25                  30

Gly Arg Arg Ile Ser Ala Arg Gly Glu Asp Gly Asp Lys Tyr Ala Gln
             35                  40                  45

Leu Leu Val Glu Thr Asp Thr Phe Gly Ser Gln Val Arg Ile Lys Gly
 50                  55                  60

Lys Glu Thr Glu Phe Tyr Leu Cys Met Asn Arg Lys Gly Lys Leu Val
 65                  70                  75                  80

Gly Lys Pro Asp Gly Thr Ser Lys Glu Cys Val Phe Ile Glu Lys Val
                 85                  90                  95

Leu Glu Asn Asn Tyr Thr Ala Leu Met Ser Ala Lys Tyr Ser Gly Trp
            100                 105                 110

Tyr Val Gly Phe Thr Lys Lys Gly Arg Pro Arg Lys Gly Pro Lys Thr
        115                 120                 125

Arg Glu Asn Gln Gln Asp Val His Phe Met Lys Arg Tyr Pro Lys Gly
    130                 135                 140

Gln Pro Glu Leu Gln Lys Pro Phe Lys Tyr Thr Thr Val Thr Lys Arg
145                 150                 155                 160

Ser Arg Arg Ile Arg Pro Thr His Pro Ala
                165                 170
```

<210> SEQ ID NO 4
<211> LENGTH: 166
<212> TYPE: PRT
<213> ORGANISM: Homo sapiens

<400> SEQUENCE: 4

```
Met Ala Arg Asp Asp Val Ser Arg Lys Gln Leu Arg Leu Tyr Gln Leu
  1               5                  10                  15

Tyr Ser Arg Thr Ser Gly Lys His Ile Gln Val Leu Gly Arg Arg Ile
                 20                  25                  30

Ser Ala Arg Gly Glu Asp Gly Asp Lys Tyr Ala Gln Leu Leu Val Glu
```

```
                    35                  40                  45
Thr Asp Thr Phe Gly Ser Gln Val Arg Ile Lys Gly Lys Glu Thr Glu
            50                  55                  60
Phe Tyr Leu Cys Met Asn Arg Lys Gly Lys Leu Val Gly Lys Pro Asp
65                  70                  75                  80
Gly Thr Ser Lys Glu Cys Val Phe Ile Glu Lys Val Leu Glu Asn Asn
                85                  90                  95
Tyr Thr Ala Leu Met Ser Ala Lys Tyr Ser Gly Trp Tyr Val Gly Phe
            100                 105                 110
Thr Lys Lys Gly Arg Pro Arg Lys Gly Pro Lys Thr Arg Glu Asn Gln
            115                 120                 125
Gln Asp Val His Phe Met Lys Arg Tyr Pro Lys Gly Gln Pro Glu Leu
        130                 135                 140
Gln Lys Pro Phe Lys Tyr Thr Thr Val Thr Lys Arg Ser Arg Arg Ile
145                 150                 155                 160
Arg Pro Thr His Pro Ala
                165

<210> SEQ ID NO 5
<211> LENGTH: 164
<212> TYPE: PRT
<213> ORGANISM: Homo sapiens

<400> SEQUENCE: 5

Met Asp Asp Val Ser Arg Lys Gln Leu Arg Leu Tyr Gln Leu Tyr Ser
1               5                   10                  15
Arg Thr Ser Gly Lys His Ile Gln Val Leu Gly Arg Arg Ile Ser Ala
            20                  25                  30
Arg Gly Glu Asp Gly Asp Lys Tyr Ala Gln Leu Leu Val Glu Thr Asp
        35                  40                  45
Thr Phe Gly Ser Gln Val Arg Ile Lys Gly Lys Glu Thr Glu Phe Tyr
    50                  55                  60
Leu Cys Met Asn Arg Lys Gly Lys Leu Val Gly Lys Pro Asp Gly Thr
65                  70                  75                  80
Ser Lys Glu Cys Val Phe Ile Glu Lys Val Leu Glu Asn Asn Tyr Thr
                85                  90                  95
Ala Leu Met Ser Ala Lys Tyr Ser Gly Trp Tyr Val Gly Phe Thr Lys
            100                 105                 110
Lys Gly Arg Pro Arg Lys Gly Pro Lys Thr Arg Glu Asn Gln Gln Asp
        115                 120                 125
Val His Phe Met Lys Arg Tyr Pro Lys Gly Gln Pro Glu Leu Gln Lys
    130                 135                 140
Pro Phe Lys Tyr Thr Thr Val Thr Lys Arg Ser Arg Arg Ile Arg Pro
145                 150                 155                 160
Thr His Pro Ala

<210> SEQ ID NO 6
<211> LENGTH: 160
<212> TYPE: PRT
<213> ORGANISM: Homo sapiens

<400> SEQUENCE: 6

Met Arg Lys Gln Leu Arg Leu Tyr Gln Leu Tyr Ser Arg Thr Ser Gly
1               5                   10                  15
Lys His Ile Gln Val Leu Gly Arg Arg Ile Ser Ala Arg Gly Glu Asp
            20                  25                  30
```

```
Gly Asp Lys Tyr Ala Gln Leu Leu Val Glu Thr Asp Thr Phe Gly Ser
            35                  40                  45

Gln Val Arg Ile Lys Gly Lys Glu Thr Glu Phe Tyr Leu Cys Met Asn
 50                  55                  60

Arg Lys Gly Lys Leu Val Gly Lys Pro Asp Gly Thr Ser Lys Glu Cys
 65                  70                  75                  80

Val Phe Ile Glu Lys Val Leu Glu Asn Asn Tyr Thr Ala Leu Met Ser
                 85                  90                  95

Ala Lys Tyr Ser Gly Trp Tyr Val Gly Phe Thr Lys Lys Gly Arg Pro
            100                 105                 110

Arg Lys Gly Pro Lys Thr Arg Glu Asn Gln Gln Asp Val His Phe Met
        115                 120                 125

Lys Arg Tyr Pro Lys Gly Gln Pro Glu Leu Gln Lys Pro Phe Lys Tyr
    130                 135                 140

Thr Thr Val Thr Lys Arg Ser Arg Arg Ile Arg Pro Thr His Pro Ala
145                 150                 155                 160

<210> SEQ ID NO 7
<211> LENGTH: 145
<212> TYPE: PRT
<213> ORGANISM: Homo sapiens

<400> SEQUENCE: 7

Met Lys His Ile Gln Val Leu Gly Arg Arg Ile Ser Ala Arg Gly Glu
 1               5                  10                  15

Asp Gly Asp Lys Tyr Ala Gln Leu Leu Val Glu Thr Asp Thr Phe Gly
                20                  25                  30

Ser Gln Val Arg Ile Lys Gly Lys Glu Thr Glu Phe Tyr Leu Cys Met
            35                  40                  45

Asn Arg Lys Gly Lys Leu Val Gly Lys Pro Asp Gly Thr Ser Lys Glu
        50                  55                  60

Cys Val Phe Ile Glu Lys Val Leu Glu Asn Asn Tyr Thr Ala Leu Met
 65                  70                  75                  80

Ser Ala Lys Tyr Ser Gly Trp Tyr Val Gly Phe Thr Lys Lys Gly Arg
                 85                  90                  95

Pro Arg Lys Gly Pro Lys Thr Arg Glu Asn Gln Gln Asp Val His Phe
            100                 105                 110

Met Lys Arg Tyr Pro Lys Gly Gln Pro Glu Leu Gln Lys Pro Phe Lys
        115                 120                 125

Tyr Thr Thr Val Thr Lys Arg Ser Arg Arg Ile Arg Pro Thr His Pro
    130                 135                 140

Ala
145

<210> SEQ ID NO 8
<211> LENGTH: 134
<212> TYPE: PRT
<213> ORGANISM: Homo sapiens

<400> SEQUENCE: 8

Met Ala Arg Gly Glu Asp Gly Asp Lys Tyr Ala Gln Leu Leu Val Glu
 1               5                  10                  15

Thr Asp Thr Phe Gly Ser Gln Val Arg Ile Lys Gly Lys Glu Thr Glu
                20                  25                  30

Phe Tyr Leu Cys Met Asn Arg Lys Gly Lys Leu Val Gly Lys Pro Asp
            35                  40                  45
```

```
Gly Thr Ser Lys Glu Cys Val Phe Ile Glu Lys Val Leu Glu Asn Asn
 50                  55                  60

Tyr Thr Ala Leu Met Ser Ala Lys Tyr Ser Gly Trp Tyr Val Gly Phe
 65                  70                  75                  80

Thr Lys Lys Gly Arg Pro Arg Lys Gly Pro Lys Thr Arg Glu Asn Gln
                 85                  90                  95

Gln Asp Val His Phe Met Lys Arg Tyr Pro Lys Gly Gln Pro Glu Leu
            100                 105                 110

Gln Lys Pro Phe Lys Tyr Thr Thr Val Thr Lys Arg Ser Arg Arg Ile
        115                 120                 125

Arg Pro Thr His Pro Ala
        130

<210> SEQ ID NO 9
<211> LENGTH: 115
<212> TYPE: PRT
<213> ORGANISM: Homo sapiens

<400> SEQUENCE: 9

Met Gly Ser Gln Val Arg Ile Lys Gly Lys Glu Thr Glu Phe Tyr Leu
  1               5                  10                  15

Cys Met Asn Arg Lys Gly Lys Leu Val Gly Lys Pro Asp Gly Thr Ser
                 20                  25                  30

Lys Glu Cys Val Phe Ile Glu Lys Val Leu Glu Asn Asn Tyr Thr Ala
             35                  40                  45

Leu Met Ser Ala Lys Tyr Ser Gly Trp Tyr Val Gly Phe Thr Lys Lys
 50                  55                  60

Gly Arg Pro Arg Lys Gly Pro Lys Thr Arg Glu Asn Gln Gln Asp Val
 65                  70                  75                  80

His Phe Met Lys Arg Tyr Pro Lys Gly Gln Pro Glu Leu Gln Lys Pro
                 85                  90                  95

Phe Lys Tyr Thr Thr Val Thr Lys Arg Ser Arg Arg Ile Arg Pro Thr
            100                 105                 110

His Pro Ala
        115

<210> SEQ ID NO 10
<211> LENGTH: 105
<212> TYPE: PRT
<213> ORGANISM: Homo sapiens

<400> SEQUENCE: 10

Met Thr Glu Phe Tyr Leu Cys Met Asn Arg Lys Gly Lys Leu Val Gly
  1               5                  10                  15

Lys Pro Asp Gly Thr Ser Lys Glu Cys Val Phe Ile Glu Lys Val Leu
                 20                  25                  30

Glu Asn Asn Tyr Thr Ala Leu Met Ser Ala Lys Tyr Ser Gly Trp Tyr
             35                  40                  45

Val Gly Phe Thr Lys Lys Gly Arg Pro Arg Lys Gly Pro Lys Thr Arg
 50                  55                  60

Glu Asn Gln Gln Asp Val His Phe Met Lys Arg Tyr Pro Lys Gly Gln
 65                  70                  75                  80

Pro Glu Leu Gln Lys Pro Phe Lys Tyr Thr Thr Val Thr Lys Arg Ser
                 85                  90                  95

Arg Arg Ile Arg Pro Thr His Pro Ala
            100                 105
```

<210> SEQ ID NO 11
<211> LENGTH: 87
<212> TYPE: PRT
<213> ORGANISM: Homo sapiens

<400> SEQUENCE: 11

```
Met Gly Thr Ser Lys Glu Cys Val Phe Ile Glu Lys Val Leu Glu Asn
1               5                   10                  15

Asn Tyr Thr Ala Leu Met Ser Ala Lys Tyr Ser Gly Trp Tyr Val Gly
                20                  25                  30

Phe Thr Lys Lys Gly Arg Pro Arg Lys Gly Pro Lys Thr Arg Glu Asn
            35                  40                  45

Gln Gln Asp Val His Phe Met Lys Arg Tyr Pro Lys Gly Gln Pro Glu
        50                  55                  60

Leu Gln Lys Pro Phe Lys Tyr Thr Thr Val Thr Lys Arg Ser Arg Arg
65                  70                  75                  80

Ile Arg Pro Thr His Pro Ala
                85
```

<210> SEQ ID NO 12
<211> LENGTH: 182
<212> TYPE: PRT
<213> ORGANISM: Mus musculus

<400> SEQUENCE: 12

```
Met Ala Glu Glu Asn Val Asp Phe Arg Ile His Val Glu Asn Gln Thr
1               5                   10                  15

Arg Ala Arg Asp Asp Val Ser Arg Lys Gln Leu Arg Leu Tyr Gln Leu
                20                  25                  30

Tyr Ser Arg Thr Ser Gly Lys His Ile Gln Val Leu Gly Arg Arg Ile
            35                  40                  45

Ser Ala Arg Gly Glu Asp Gly Asp Lys Tyr Ala Gln Leu Leu Val Glu
        50                  55                  60

Thr Asp Thr Phe Gly Ser Gln Val Arg Ile Lys Gly Lys Glu Thr Glu
65                  70                  75                  80

Phe Tyr Leu Cys Met Asn Arg Lys Gly Lys Leu Val Gly Lys Pro Asp
                85                  90                  95

Gly Thr Ser Lys Glu Cys Val Phe Ile Glu Lys Val Leu Glu Asn Asn
                100                 105                 110

Tyr Thr Ala Leu Met Ser Ala Lys Tyr Ser Gly Trp Tyr Val Gly Phe
            115                 120                 125

Thr Lys Lys Gly Arg Pro Arg Lys Gly Pro Lys Thr Arg Glu Asn Gln
        130                 135                 140

Gln Asp Val His Phe Met Lys Arg Tyr Pro Lys Gly Gln Ala Glu Leu
145                 150                 155                 160

Gln Lys Pro Phe Lys Tyr Thr Thr Val Thr Lys Arg Ser Arg Arg Ile
                165                 170                 175

Arg Pro Thr His Pro Gly
            180
```

<210> SEQ ID NO 13
<211> LENGTH: 178
<212> TYPE: PRT
<213> ORGANISM: Mus musculus

<400> SEQUENCE: 13

Met Val Asp Phe Arg Ile His Val Glu Asn Gln Thr Arg Ala Arg Asp
1               5                   10                  15

Asp Val Ser Arg Lys Gln Leu Arg Leu Tyr Gln Leu Tyr Ser Arg Thr
            20                  25                  30

Ser Gly Lys His Ile Gln Val Leu Gly Arg Arg Ile Ser Ala Arg Gly
            35                  40                  45

Glu Asp Gly Asp Lys Tyr Ala Gln Leu Leu Val Glu Thr Asp Thr Phe
50                  55                  60

Gly Ser Gln Val Arg Ile Lys Gly Lys Glu Thr Glu Phe Tyr Leu Cys
65                  70                  75                  80

Met Asn Arg Lys Gly Lys Leu Val Gly Lys Pro Asp Gly Thr Ser Lys
                85                  90                  95

Glu Cys Val Phe Ile Glu Lys Val Leu Glu Asn Asn Tyr Thr Ala Leu
            100                 105                 110

Met Ser Ala Lys Tyr Ser Gly Trp Tyr Val Gly Phe Thr Lys Lys Gly
            115                 120                 125

Arg Pro Arg Lys Gly Pro Lys Thr Arg Glu Asn Gln Gln Asp Val His
            130                 135                 140

Phe Met Lys Arg Tyr Pro Lys Gly Gln Ala Glu Leu Gln Lys Pro Phe
145                 150                 155                 160

Lys Tyr Thr Thr Val Thr Lys Arg Ser Arg Ile Arg Pro Thr His
                165                 170                 175

Pro Gly

<210> SEQ ID NO 14
<211> LENGTH: 170
<212> TYPE: PRT
<213> ORGANISM: Mus musculus

<400> SEQUENCE: 14

Met Asn Gln Thr Arg Ala Arg Asp Asp Val Ser Arg Lys Gln Leu Arg
1               5                   10                  15

Leu Tyr Gln Leu Tyr Ser Arg Thr Ser Gly Lys His Ile Gln Val Leu
            20                  25                  30

Gly Arg Arg Ile Ser Ala Arg Gly Glu Asp Gly Asp Lys Tyr Ala Gln
            35                  40                  45

Leu Leu Val Glu Thr Asp Thr Phe Gly Ser Gln Val Arg Ile Lys Gly
        50                  55                  60

Lys Glu Thr Glu Phe Tyr Leu Cys Met Asn Arg Lys Gly Lys Leu Val
65                  70                  75                  80

Gly Lys Pro Asp Gly Thr Ser Lys Glu Cys Val Phe Ile Glu Lys Val
                85                  90                  95

Leu Glu Asn Asn Tyr Thr Ala Leu Met Ser Ala Lys Tyr Ser Gly Trp
            100                 105                 110

Tyr Val Gly Phe Thr Lys Lys Gly Arg Pro Arg Lys Gly Pro Lys Thr
            115                 120                 125

Arg Glu Asn Gln Gln Asp Val His Phe Met Lys Arg Tyr Pro Lys Gly
            130                 135                 140

Gln Ala Glu Leu Gln Lys Pro Phe Lys Tyr Thr Thr Val Thr Lys Arg
145                 150                 155                 160

Ser Arg Arg Ile Arg Pro Thr His Pro Gly
                165                 170

<210> SEQ ID NO 15
<211> LENGTH: 166

```
<212> TYPE: PRT
<213> ORGANISM: Mus musculus

<400> SEQUENCE: 15

Met Ala Arg Asp Asp Val Ser Arg Lys Gln Leu Arg Leu Tyr Gln Leu
1               5                   10                  15

Tyr Ser Arg Thr Ser Gly Lys His Ile Gln Val Leu Gly Arg Arg Ile
            20                  25                  30

Ser Ala Arg Gly Glu Asp Gly Asp Lys Tyr Ala Gln Leu Leu Val Glu
        35                  40                  45

Thr Asp Thr Phe Gly Ser Gln Val Arg Ile Lys Gly Lys Glu Thr Glu
50                  55                  60

Phe Tyr Leu Cys Met Asn Arg Lys Gly Lys Leu Val Gly Lys Pro Asp
65                  70                  75                  80

Gly Thr Ser Lys Glu Cys Val Phe Ile Glu Lys Val Leu Glu Asn Asn
                85                  90                  95

Tyr Thr Ala Leu Met Ser Ala Lys Tyr Ser Gly Trp Tyr Val Gly Phe
                100                 105                 110

Thr Lys Lys Gly Arg Pro Arg Lys Gly Pro Lys Thr Arg Glu Asn Gln
            115                 120                 125

Gln Asp Val His Phe Met Lys Arg Tyr Pro Lys Gly Gln Ala Glu Leu
130                 135                 140

Gln Lys Pro Phe Lys Tyr Thr Thr Val Thr Lys Arg Ser Arg Arg Ile
145                 150                 155                 160

Arg Pro Thr His Pro Gly
                165

<210> SEQ ID NO 16
<211> LENGTH: 164
<212> TYPE: PRT
<213> ORGANISM: Mus musculus

<400> SEQUENCE: 16

Met Asp Asp Val Ser Arg Lys Gln Leu Arg Leu Tyr Gln Leu Tyr Ser
1               5                   10                  15

Arg Thr Ser Gly Lys His Ile Gln Val Leu Gly Arg Arg Ile Ser Ala
            20                  25                  30

Arg Gly Glu Asp Gly Asp Lys Tyr Ala Gln Leu Leu Val Glu Thr Asp
        35                  40                  45

Thr Phe Gly Ser Gln Val Arg Ile Lys Gly Lys Glu Thr Glu Phe Tyr
50                  55                  60

Leu Cys Met Asn Arg Lys Gly Lys Leu Val Gly Lys Pro Asp Gly Thr
65                  70                  75                  80

Ser Lys Glu Cys Val Phe Ile Glu Lys Val Leu Glu Asn Asn Tyr Thr
                85                  90                  95

Ala Leu Met Ser Ala Lys Tyr Ser Gly Trp Tyr Val Gly Phe Thr Lys
                100                 105                 110

Lys Gly Arg Pro Arg Lys Gly Pro Lys Thr Arg Glu Asn Gln Gln Asp
            115                 120                 125

Val His Phe Met Lys Arg Tyr Pro Lys Gly Gln Ala Glu Leu Gln Lys
130                 135                 140

Pro Phe Lys Tyr Thr Thr Val Thr Lys Arg Ser Arg Arg Ile Arg Pro
145                 150                 155                 160

Thr His Pro Gly
```

<210> SEQ ID NO 17
<211> LENGTH: 160
<212> TYPE: PRT
<213> ORGANISM: Mus musculus

<400> SEQUENCE: 17

Met Arg Lys Gln Leu Arg Leu Tyr Gln Leu Tyr Ser Arg Thr Ser Gly
1               5                   10                  15

Lys His Ile Gln Val Leu Gly Arg Arg Ile Ser Ala Arg Gly Glu Asp
            20                  25                  30

Gly Asp Lys Tyr Ala Gln Leu Leu Val Glu Thr Asp Thr Phe Gly Ser
        35                  40                  45

Gln Val Arg Ile Lys Gly Lys Glu Thr Glu Phe Tyr Leu Cys Met Asn
    50                  55                  60

Arg Lys Gly Lys Leu Val Gly Lys Pro Asp Gly Thr Ser Lys Glu Cys
65                  70                  75                  80

Val Phe Ile Glu Lys Val Leu Glu Asn Asn Tyr Thr Ala Leu Met Ser
                85                  90                  95

Ala Lys Tyr Ser Gly Trp Tyr Val Gly Phe Thr Lys Lys Gly Arg Pro
            100                 105                 110

Arg Lys Gly Pro Lys Thr Arg Glu Asn Gln Gln Asp Val His Phe Met
        115                 120                 125

Lys Arg Tyr Pro Lys Gly Gln Ala Glu Leu Gln Lys Pro Phe Lys Tyr
    130                 135                 140

Thr Thr Val Thr Lys Arg Ser Arg Arg Ile Arg Pro Thr His Pro Gly
145                 150                 155                 160

<210> SEQ ID NO 18
<211> LENGTH: 145
<212> TYPE: PRT
<213> ORGANISM: Mus musculus

<400> SEQUENCE: 18

Met Lys His Ile Gln Val Leu Gly Arg Arg Ile Ser Ala Arg Gly Glu
1               5                   10                  15

Asp Gly Asp Lys Tyr Ala Gln Leu Leu Val Glu Thr Asp Thr Phe Gly
            20                  25                  30

Ser Gln Val Arg Ile Lys Gly Lys Glu Thr Glu Phe Tyr Leu Cys Met
        35                  40                  45

Asn Arg Lys Gly Lys Leu Val Gly Lys Pro Asp Gly Thr Ser Lys Glu
    50                  55                  60

Cys Val Phe Ile Glu Lys Val Leu Glu Asn Asn Tyr Thr Ala Leu Met
65                  70                  75                  80

Ser Ala Lys Tyr Ser Gly Trp Tyr Val Gly Phe Thr Lys Lys Gly Arg
                85                  90                  95

Pro Arg Lys Gly Pro Lys Thr Arg Glu Asn Gln Gln Asp Val His Phe
            100                 105                 110

Met Lys Arg Tyr Pro Lys Gly Gln Ala Glu Leu Gln Lys Pro Phe Lys
        115                 120                 125

Tyr Thr Thr Val Thr Lys Arg Ser Arg Arg Ile Arg Pro Thr His Pro
    130                 135                 140

Gly
145

<210> SEQ ID NO 19
<211> LENGTH: 134
<212> TYPE: PRT

<213> ORGANISM: Mus musculus

<400> SEQUENCE: 19

Met Ala Arg Gly Glu Asp Gly Asp Lys Tyr Ala Gln Leu Leu Val Glu
1               5                   10                  15

Thr Asp Thr Phe Gly Ser Gln Val Arg Ile Lys Gly Lys Glu Thr Glu
                20                  25                  30

Phe Tyr Leu Cys Met Asn Arg Lys Gly Lys Leu Val Gly Lys Pro Asp
            35                  40                  45

Gly Thr Ser Lys Glu Cys Val Phe Ile Glu Lys Val Leu Glu Asn Asn
        50                  55                  60

Tyr Thr Ala Leu Met Ser Ala Lys Tyr Ser Gly Trp Tyr Val Gly Phe
65                  70                  75                  80

Thr Lys Lys Gly Arg Pro Arg Lys Gly Pro Lys Thr Arg Glu Asn Gln
                85                  90                  95

Gln Asp Val His Phe Met Lys Arg Tyr Pro Lys Gly Gln Ala Glu Leu
                100                 105                 110

Gln Lys Pro Phe Lys Tyr Thr Thr Val Thr Lys Arg Ser Arg Arg Ile
            115                 120                 125

Arg Pro Thr His Pro Gly
            130

<210> SEQ ID NO 20
<211> LENGTH: 115
<212> TYPE: PRT
<213> ORGANISM: Mus musculus

<400> SEQUENCE: 20

Met Gly Ser Gln Val Arg Ile Lys Gly Lys Glu Thr Glu Phe Tyr Leu
1               5                   10                  15

Cys Met Asn Arg Lys Gly Lys Leu Val Gly Lys Pro Asp Gly Thr Ser
                20                  25                  30

Lys Glu Cys Val Phe Ile Glu Lys Val Leu Glu Asn Asn Tyr Thr Ala
            35                  40                  45

Leu Met Ser Ala Lys Tyr Ser Gly Trp Tyr Val Gly Phe Thr Lys Lys
        50                  55                  60

Gly Arg Pro Arg Lys Gly Pro Lys Thr Arg Glu Asn Gln Gln Asp Val
65                  70                  75                  80

His Phe Met Lys Arg Tyr Pro Lys Gly Gln Ala Glu Leu Gln Lys Pro
                85                  90                  95

Phe Lys Tyr Thr Thr Val Thr Lys Arg Ser Arg Arg Ile Arg Pro Thr
                100                 105                 110

His Pro Gly
        115

<210> SEQ ID NO 21
<211> LENGTH: 105
<212> TYPE: PRT
<213> ORGANISM: Mus musculus

<400> SEQUENCE: 21

Met Thr Glu Phe Tyr Leu Cys Met Asn Arg Lys Gly Lys Leu Val Gly
1               5                   10                  15

Lys Pro Asp Gly Thr Ser Lys Glu Cys Val Phe Ile Glu Lys Val Leu
                20                  25                  30

Glu Asn Asn Tyr Thr Ala Leu Met Ser Ala Lys Tyr Ser Gly Trp Tyr
            35                  40                  45

Val Gly Phe Thr Lys Lys Gly Arg Pro Arg Lys Gly Pro Lys Thr Arg
          50                  55                  60

Glu Asn Gln Gln Asp Val His Phe Met Lys Arg Tyr Pro Lys Gly Gln
 65                  70                  75                  80

Ala Glu Leu Gln Lys Pro Phe Lys Tyr Thr Thr Val Thr Lys Arg Ser
                 85                  90                  95

Arg Arg Ile Arg Pro Thr His Pro Gly
            100                 105

<210> SEQ ID NO 22
<211> LENGTH: 87
<212> TYPE: PRT
<213> ORGANISM: Mus musculus

<400> SEQUENCE: 22

Met Gly Thr Ser Lys Glu Cys Val Phe Ile Glu Lys Val Leu Glu Asn
 1               5                  10                  15

Asn Tyr Thr Ala Leu Met Ser Ala Lys Tyr Ser Gly Trp Tyr Val Gly
                 20                  25                  30

Phe Thr Lys Lys Gly Arg Pro Arg Lys Gly Pro Lys Thr Arg Glu Asn
             35                  40                  45

Gln Gln Asp Val His Phe Met Lys Arg Tyr Pro Lys Gly Gln Ala Glu
         50                  55                  60

Leu Gln Lys Pro Phe Lys Tyr Thr Thr Val Thr Lys Arg Ser Arg Arg
 65                  70                  75                  80

Ile Arg Pro Thr His Pro Gly
                 85

<210> SEQ ID NO 23
<211> LENGTH: 549
<212> TYPE: DNA
<213> ORGANISM: Homo sapiens

<400> SEQUENCE: 23
atggccgagg agaacgtgga cttccgcatc cacgtggaga accagacgcg ggctcgggac      60
gatgtgagcc gtaagcagct gcggctgtac cagctctaca gccggaccag tgggaaacac     120
atccaggtcc tgggccgcag gatcagtgcc cgcggcgagg atgggacaa gtatgcccag      180
ctcctagtgg agacagacac cttcggtagt caagtccgga tcaagggcaa ggagacggaa     240
ttctacctgt gcatgaaccg caaaggcaag ctcgtgggga gcccgatgg caccagcaag      300
gagtgtgtgt tcatcgagaa ggttctggag aacaactaca cggccctgat gtcggctaag     360
tactccggct ggtacgtggg cttcaccaag aaggggcggc cgcggaaggg ccccaagacc     420
cgggagaacc agcaggacgt gcatttcatg aagcgctacc ccaaggggca gccggagctt     480
cagaagccct tcaagtacac gacggtgacc aagaggtccc gtcggatccg gcccacacac     540
cctgcctag                                                            549

<210> SEQ ID NO 24
<211> LENGTH: 537
<212> TYPE: DNA
<213> ORGANISM: Homo sapiens

<400> SEQUENCE: 24
atggtggact tccgcatcca cgtggagaac cagacgcggg ctcgggacga tgtgagccgt       60
aagcagctgc ggctgtacca gctctacagc cggaccagtg ggaaacacat ccaggtcctg     120

| | |
|---|---|
| ggccgcagga tcagtgcccg cggcgaggat ggggacaagt atgcccagct cctagtggag | 180 |
| acagacacct tcggtagtca agtccggatc aagggcaagg agacggaatt ctacctgtgc | 240 |
| atgaaccgca aggcaagct cgtggggaag cccgatggca ccagcaagga gtgtgtgttc | 300 |
| atcgagaagg ttctggagaa caactacacg gccctgatgt cggctaagta ctccggctgg | 360 |
| tacgtgggct tcaccaagaa ggggcggccg cggaagggcc caagacccg ggagaaccag | 420 |
| caggacgtgc atttcatgaa gcgctacccc aagggggcagc cggagcttca gaagcccttc | 480 |
| aagtacacga cggtgaccaa gaggtcccgt cggatccggc ccacacaccc tgcctag | 537 |

<210> SEQ ID NO 25
<211> LENGTH: 513
<212> TYPE: DNA
<213> ORGANISM: Homo sapiens

<400> SEQUENCE: 25

| | |
|---|---|
| atgaaccaga cgcgggctcg ggacgatgtg agccgtaagc agctgcggct gtaccagctc | 60 |
| tacagccgga ccagtgggaa acacatccag gtcctgggcc gcaggatcag tgcccgcggc | 120 |
| gaggatgggg acaagtatgc ccagctccta gtggagacag acccttcgg tagtcaagtc | 180 |
| cggatcaagg gcaaggagac ggaattctac ctgtgcatga accgcaaagg caagctcgtg | 240 |
| gggaagcccg atggcaccag caaggagtgt gtgttcatcg agaaggttct ggagaacaac | 300 |
| tacacggccc tgatgtcggc taagtactcc ggctggtacg tgggcttcac caagaagggg | 360 |
| cggccgcgga agggccccaa gacccgggag aaccagcagg acgtgcattt catgaagcgc | 420 |
| taccccaagg ggcagccgga gcttcagaag cccttcaagt acacgacggt gaccaagagg | 480 |
| tcccgtcgga tccggcccac acccctgcc tag | 513 |

<210> SEQ ID NO 26
<211> LENGTH: 501
<212> TYPE: DNA
<213> ORGANISM: Homo sapiens

<400> SEQUENCE: 26

| | |
|---|---|
| atggctcggg acgatgtgag ccgtaagcag ctgcggctgt accagctcta cagccggacc | 60 |
| agtgggaaac acatccaggt cctgggccgc aggatcagtg cccgcggcga ggatggggac | 120 |
| aagtatgccc agctcctagt ggagacagac accttcggta gtcaagtccg gatcaagggc | 180 |
| aaggagacgg aattctacct gtgcatgaac cgcaaaggca agctcgtggg gaagcccgat | 240 |
| ggcaccagca aggagtgtgt gttcatcgag aaggttctgg agaacaacta cacggccctg | 300 |
| atgtcggcta agtactccgg ctggtacgtg gcttcacca agaaggggcg gccgcggaag | 360 |
| ggccccaaga cccgggagaa ccagcaggac gtgcatttca tgaagcgcta ccccaagggg | 420 |
| cagccggagc ttcagaagcc cttcaagtac acgacggtga ccaagaggtc ccgtcggatc | 480 |
| cggcccacac accctgccta g | 501 |

<210> SEQ ID NO 27
<211> LENGTH: 492
<212> TYPE: DNA
<213> ORGANISM: Homo sapiens

<400> SEQUENCE: 27

| | |
|---|---|
| atggatgtga gccgtaagca gctgcggctg taccagctct acagccggac cagtgggaaa | 60 |
| cacatccagg tcctgggccg caggatcagt gcccgcggcg aggatgggga caagtatgcc | 120 |
| cagctcctag tggagacaga caccttcggt agtcaagtcc ggatcaaggg caaggagacg | 180 |

```
gaattctacc tgtgcatgaa ccgcaaaggc aagctcgtgg ggaagcccga tggcaccagc    240
aaggagtgtg tgttcatcga aaggttctg gagaacaact acacggccct gatgtcggct      300
aagtactccg gctggtacgt gggcttcacc aagaaggggc ggccgcggaa gggccccaag     360
acccgggaga accagcagga cgtgcatttc atgaagcgct accccaaggg gcagccggag    420
cttcagaagc ccttcaagta cacgacggtg accaagaggt cccgtcggat ccggcccaca    480
caccctgcct ag                                                        492

<210> SEQ ID NO 28
<211> LENGTH: 483
<212> TYPE: DNA
<213> ORGANISM: Homo sapiens

<400> SEQUENCE: 28
atgcgtaagc agctgcggct gtaccagctc tacagccgga ccagtgggaa acacatccag     60
gtcctgggcc gcaggatcag tgcccgcggc gaggatgggg acaagtatgc ccagctccta   120
gtggagacag acaccttcgg tagtcaagtc cggatcaagg caaggagac ggaattctac    180 ctgtgcatga accgcaaagg caagctcgtg gggaagcccg atggcaccag caaggagtgt   240
gtgttcatcg agaaggttct ggagaacaac tacacggccc tgatgtcggc taagtactcc    300
ggctggtacg tgggcttcac caagaagggg cggccgcgga agggccccaa gacccgggag    360
aaccagcagg acgtgcattt catgaagcgc taccccaagg gcagccgga gcttcagaag     420 cccttcaagt cacgacggt gaccaagagg tcccgtcgga tccggcccac acaccctgcc     480
tag                                                                  483

<210> SEQ ID NO 29
<211> LENGTH: 438
<212> TYPE: DNA
<213> ORGANISM: Homo sapiens

<400> SEQUENCE: 29
atgaaacaca tccaggtcct gggccgcagg atcagtgccc gcggcgagga tggggacaag     60
tatgcccagc tcctagtgga gacagacacc ttcggtagtc aagtccggat caagggcaag    120
gagacggaat ctacctgtg catgaaccgc aaaggcaagc tcgtggggaa gcccgatggc     180
accagcaagg agtgtgtgtt catcgagaag gttctggaga caactacac ggccctgatg    240 tcggctaagt actccggctg gtacgtgggc ttcaccaaga aggggcggcc gcggaagggc    300
ccaagacccc gggagaacca gcaggacgtg catttcatga gcgctacccc aaggggcag    360 ccggagcttc agaagccctt caagtacacg acggtgacca agaggtcccg tcggatccgg    420
cccacacacc ctgcctag                                                  438

<210> SEQ ID NO 30
<211> LENGTH: 405
<212> TYPE: DNA
<213> ORGANISM: Homo sapiens

<400> SEQUENCE: 30
atggcccgcg gcgaggatgg ggacaagtat gcccagctcc tagtggagac agacaccttc     60
ggtagtcaag tccggatcaa gggcaaggag acggaattct acctgtgcat gaaccgcaaa    120
ggcaagctcg tggggaagcc cgatggcacc agcaaggagt gtgtgttcat cgagaaggtt    180
ctggagaaca actacacggc cctgatgtcg gctaagtact ccggctggta cgtgggcttc    240
```

| | |
|---|---:|
| accaagaagg ggcggccgcg aagggcccc aagacccggg agaaccagca ggacgtgcat | 300 |
| ttcatgaagc gctaccccaa ggggcagccg gagcttcaga agcccttcaa gtacacgacg | 360 |
| gtgaccaaga ggtcccgtcg gatccggccc acacaccctg cctag | 405 |

<210> SEQ ID NO 31
<211> LENGTH: 348
<212> TYPE: DNA
<213> ORGANISM: Homo sapiens

<400> SEQUENCE: 31

| | |
|---|---:|
| atgggtagtc aagtccggat caagggcaag gagacggaat tctacctgtg catgaaccgc | 60 |
| aaaggcaagc tcgtggggaa gcccgatggc accagcaagg agtgtgtgtt catcgagaag | 120 |
| gttctggaga caactacac ggccctgatg tcggctaagt actccggctg gtacgtgggc | 180 |
| ttcaccaaga aggggcggcc gcggaagggc ccaagaccc gggagaacca gcaggacgtg | 240 |
| catttcatga gcgctaccc caaggggcag ccggagcttc agaagccctt caagtacacg | 300 |
| acggtgacca agaggtcccg tcggatccgg cccacacacc ctgcctag | 348 |

<210> SEQ ID NO 32
<211> LENGTH: 318
<212> TYPE: DNA
<213> ORGANISM: Homo sapiens

<400> SEQUENCE: 32

| | |
|---|---:|
| atgacggaat tctacctgtg catgaaccgc aaaggcaagc tcgtggggaa gcccgatggc | 60 |
| accagcaagg agtgtgtgtt catcgagaag gttctggaga caactacac ggccctgatg | 120 |
| tcggctaagt actccggctg gtacgtgggc ttcaccaaga aggggcggcc gcggaagggc | 180 |
| ccaagaccc gggagaacca gcaggacgtg catttcatga gcgctaccc caaggggcag | 240 |
| ccggagcttc agaagccctt caagtacacg acggtgacca agaggtcccg tcggatccgg | 300 |
| cccacacacc ctgcctag | 318 |

<210> SEQ ID NO 33
<211> LENGTH: 264
<212> TYPE: DNA
<213> ORGANISM: Homo sapiens

<400> SEQUENCE: 33

| | |
|---|---:|
| atgggcacca gcaaggagtg tgtgttcatc gagaaggttc tggagaacaa ctacacggcc | 60 |
| ctgatgtcgg ctaagtactc cggctggtac gtgggcttca ccaagaaggg gcggccgcgg | 120 |
| aagggcccca agacccggga gaaccagcag gacgtgcatt tcatgaagcg ctaccccaag | 180 |
| gggcagccgg agcttcagaa gcccttcaag tacacgacgg tgaccaagag gtcccgtcgg | 240 |
| atccggccca cacccctgc ctag | 264 |

<210> SEQ ID NO 34
<211> LENGTH: 549
<212> TYPE: DNA
<213> ORGANISM: Mus musculus

<400> SEQUENCE: 34

| | |
|---|---:|
| atggccgagg agaatgtgga cttccgcatc cacgtggaga accagacgcg ggctcgagat | 60 |
| gatgtgagtc ggaagcagct gcgcttgtac cagctctata gcaggaccag tgggaagcac | 120 |
| attcaagtcc tggccgtag gatcagtgcc cgtggcgagg acggggacaa gtatgcccag | 180 |
| ctcctagtgg agacagatac cttcgggagt caagtccgga tcaagggcaa ggagacagaa | 240 |

-continued

| | |
|---|---|
| ttctacctgt gtatgaaccg aaaaggcaag ctcgtgggga agcctgatgg tactagcaag | 300 |
| gagtgcgtgt tcattgagaa ggttctggaa aacaactaca cggccctgat gtctgccaag | 360 |
| tactctggtt ggtatgtggg cttcaccaag aaggggcggc ctcgcaaggg tcccaagacc | 420 |
| cgcgagaacc agcaagatgt acacttcatg aagcgttacc ccaagggaca ggccgagctg | 480 |
| cagaagccct tcaaatacac cacagtcacc aagcgatccc ggcggatccg ccccactcac | 540 |
| cccggctag | 549 |

<210> SEQ ID NO 35
<211> LENGTH: 537
<212> TYPE: DNA
<213> ORGANISM: Mus musculus

<400> SEQUENCE: 35

| | |
|---|---|
| atggtggact ccgcatcca cgtggagaac cagacgcggg ctcgagatga tgtgagtcgg | 60 |
| aagcagctgc gcttgtacca gctctatagc aggaccagtg ggaagcacat tcaagtcctg | 120 |
| ggccgtagga tcagtgcccg tggcgaggac ggggacaagt atgcccagct cctagtggag | 180 |
| acagatacct tcgggagtca agtccggatc aagggcaagg agacagaatt ctacctgtgt | 240 |
| atgaaccgaa aaggcaagct cgtggggaag cctgatggta ctagcaagga gtgcgtgttc | 300 |
| attgagaagg ttctggaaaa caactacacg gccctgatgt ctgccaagta ctctggttgg | 360 |
| tatgtgggct tcaccaagaa ggggcggcct cgcaagggtc ccaagacccg cgagaaccag | 420 |
| caagatgtac acttcatgaa gcgttacccc aagggacagg ccgagctgca gaagcccttc | 480 |
| aaatacacca cagtcaccaa gcgatcccgg cggatccgcc ccactcaccc cggctag | 537 |

<210> SEQ ID NO 36
<211> LENGTH: 513
<212> TYPE: DNA
<213> ORGANISM: Mus musculus

<400> SEQUENCE: 36

| | |
|---|---|
| atgaaccaga cgcgggctcg agatgatgtg agtcggaagc agctgcgctt gtaccagctc | 60 |
| tatagcagga ccagtgggaa gcacattcaa gtcctgggcc gtaggatcag tgcccgtggc | 120 |
| gaggacgggg acaagtatgc ccagctccta gtggagacag ataccttcgg gagtcaagtc | 180 |
| cggatcaagg gcaaggagac agaattctac ctgtgtatga accgaaaagg caagctcgtg | 240 |
| gggaagcctg atggtactag caaggagtgc gtgttcattg agaaggttct ggaaaacaac | 300 |
| tacacggccc tgatgtctgc caagtactct ggttggtatg tgggcttcac caagaagggg | 360 |
| cggcctcgca agggtcccaa gacccgcgag aaccagcaag atgtacactt catgaagcgt | 420 |
| taccccaagg acaggccga gctgcagaag cccttcaaat acaccacagt caccaagcga | 480 |
| tcccggcgga tccgccccac tcaccccggc tag | 513 |

<210> SEQ ID NO 37
<211> LENGTH: 501
<212> TYPE: DNA
<213> ORGANISM: Mus musculus

<400> SEQUENCE: 37

| | |
|---|---|
| atggctcgag atgatgtgag tcggaagcag ctgcgcttgt accagctcta tagcaggacc | 60 |
| agtgggaagc acattcaagt cctgggccgt aggatcagtg cccgtggcga ggacggggac | 120 |
| aagtatgccc agctcctagt ggagacagat accttcggga gtcaagtccg gatcaagggc | 180 |

```
aaggagacag aattctacct gtgtatgaac cgaaaaggca agctcgtggg aagcctgat      240 ggtactagca aggagtgcgt gttcattgag aaggttctgg aaaacaacta cacggccctg    300
atgtctgcca agtactctgg ttggtatgtg ggcttcacca agaaggggcg gcctcgcaag    360
ggtcccaaga cccgcgagaa ccagcaagat gtacacttca tgaagcgtta ccccaaggga    420
caggccgagc tgcagaagcc cttcaaatac accacagtca ccaagcgatc ccggcggatc    480
cgccccactc accccggcta g                                              501

<210> SEQ ID NO 38
<211> LENGTH: 495
<212> TYPE: DNA
<213> ORGANISM: Mus musculus

<400> SEQUENCE: 38
atggatgatg tgagtcggaa gcagctgcgc ttgtaccagc tctatagcag gaccagtggg     60
aagcacattc aagtcctggg ccgtaggatc agtgcccgtg gcgaggacgg ggacaagtat    120
gcccagctcc tagtggagac agataccttc gggagtcaag tccggatcaa gggcaaggag    180
acagaattct acctgtgtat gaaccgaaaa ggcaagctcg tggggaagcc tgatggtact    240
agcaaggagt gcgtgttcat tgagaaggtt ctggaaaaca actacacggc cctgatgtct    300
gccaagtact ctggttggta tgtgggcttc accaagaagg gcggcctcg caagggtccc    360 aagacccgcg agaaccagca agatgtacac ttcatgaagc gttaccccaa gggacaggcc    420
gagctgcaga agcccttcaa atacaccaca gtcaccaagc gatcccggcg gatccgcccc    480
actcaccccg gctag                                                    495

<210> SEQ ID NO 39
<211> LENGTH: 483
<212> TYPE: DNA
<213> ORGANISM: Mus musculus

<400> SEQUENCE: 39
atgcggaagc agctgcgctt gtaccagctc tatagcagga ccagtgggaa gcacattcaa     60
gtcctgggcc gtaggatcag tgcccgtggc gaggacgggg acaagtatgc ccagctccta    120
gtggagacag ataccttcgg gagtcaagtc cggatcaagg gcaaggagac agaattctac    180
ctgtgtatga accgaaaagg caagctcgtg gggaagcctg atggtactag caaggagtgc    240
gtgttcattg agaaggttct ggaaaacaac tacacggccc tgatgtctgc caagtactct    300
ggttggtatg tgggcttcac caagaagggg cggcctcgca agggtcccaa gacccgcgag    360
aaccagcaag atgtacactt catgaagcgt taccccaagg gacaggccga gctgcagaag    420
cccttcaaat acaccacagt caccaagcga tcccggcgga tccgccccac tcaccccggc    480
tag                                                                 483

<210> SEQ ID NO 40
<211> LENGTH: 438
<212> TYPE: DNA
<213> ORGANISM: Mus musculus

<400> SEQUENCE: 40
atgaagcaca ttcaagtcct gggccgtagg atcagtgccc gtggcgagga cggggacaag     60
tatgcccagc tcctagtgga gacagatacc ttcgggagtc aagtccggat caagggcaag    120 agacagaat tctacctgtg tatgaaccga aaaggcaagc tcgtgggaa gcctgatggt     180 actagcaagg agtgcgtgtt cattgagaag gttctggaaa acaactacac ggccctgatg    240
```

```
tctgccaagt actctggttg gtatgtgggc ttcaccaaga aggggcggcc tcgcaagggt       300
cccaagaccc gcgagaacca gcaagatgta cacttcatga agcgttaccc caagggacag       360
gccgagctgc agaagccctt caaatacacc acagtcacca gcgatcccg gcggatccgc        420 cccactcacc ccggctag                                                      438

<210> SEQ ID NO 41
<211> LENGTH: 405
<212> TYPE: DNA
<213> ORGANISM: Mus musculus

<400> SEQUENCE: 41
atggcccgtg gcgaggacgg ggacaagtat gcccagctcc tagtggagac agataccttc        60
gggagtcaag tccggatcaa gggcaaggag acagaattct acctgtgtat gaaccgaaaa       120
ggcaagctcg tggggaagcc tgatggtact agcaaggagt gcgtgttcat tgagaaggtt       180
ctggaaaaca actacacggc cctgatgtct gccaagtact ctggttggta tgtgggcttc       240
accaagaagg gcggcctcg caagggtccc aagacccgcg agaaccagca agatgtacac        300
ttcatgaagc gttaccccaa gggacaggcc gagctgcaga agcccttcaa atacaccaca       360
gtcaccaagc gatcccggcg gatccgcccc actcacccccg gctag                      405

<210> SEQ ID NO 42
<211> LENGTH: 348
<212> TYPE: DNA
<213> ORGANISM: Mus musculus

<400> SEQUENCE: 42
atggggagtc aagtccggat caagggcaag gagacagaat ctacctgtgt atgaaccga         60 aaaggcaagc tcgtggggaa gcctgatggt actagcaagg agtgcgtgtt cattgagaag       120
gttctggaaa acaactacac ggccctgatg tctgccaagt actctggttg gtatgtgggc       180
ttcaccaaga aggggcggcc tcgcaagggt cccaagaccc gcgagaacca gcaagatgta       240
cacttcatga agcgttaccc caagggacag gccgagctgc agaagccctt caaatacacc       300
acagtcacca gcgatcccg gcggatccgc cccactcacc ccggctag                     348

<210> SEQ ID NO 43
<211> LENGTH: 318
<212> TYPE: DNA
<213> ORGANISM: Mus musculus

<400> SEQUENCE: 43
atgacagaat ctacctgtgt atgaaccga aaaggcaagc tcgtggggaa gcctgatggt         60
actagcaagg agtgcgtgtt cattgagaag gttctggaaa acaactacac ggccctgatg       120
tctgccaagt actctggttg gtatgtgggc ttcaccaaga aggggcggcc tcgcaagggt       180
cccaagaccc gcgagaacca gcaagatgta cacttcatga agcgttaccc caagggacag       240
gccgagctgc agaagccctt caaatacacc acagtcacca gcgatcccg gcggatccgc        300 cccactcacc ccggctag                                                      318

<210> SEQ ID NO 44
<211> LENGTH: 264
<212> TYPE: DNA
<213> ORGANISM: Mus musculus

<400> SEQUENCE: 44
```

```
atgggtacta gcaaggagtg cgtgttcatt gagaaggttc tggaaaacaa ctacacggcc      60
ctgatgtctg ccaagtactc tggttggtat gtgggcttca ccaagaaggg gcggcctcgc     120
aagggtccca agacccgcga gaaccagcaa gatgtacact tcatgaagcg ttaccccaag     180
ggacaggccg agctgcagaa gcccttcaaa tacaccacag tcaccaagcg atcccggcgg     240
atccgcccca ctcaccccgg ctag                                            264
```

<210> SEQ ID NO 45
<211> LENGTH: 31
<212> TYPE: PRT
<213> ORGANISM: Artificial
<220> FEATURE:
<223> OTHER INFORMATION: FLAG-His tag

<400> SEQUENCE: 45

```
Ala Arg Asp Tyr Lys Asp His Asp Gly Asp Tyr Lys Asp His Asp Ile
1               5                   10                  15

Asp Tyr Lys Asp Asp Asp Asp Lys Gly His His His His His
            20                  25                  30
```

<210> SEQ ID NO 46
<211> LENGTH: 96
<212> TYPE: DNA
<213> ORGANISM: Artificial
<220> FEATURE:
<223> OTHER INFORMATION: FLAG-His tag

<400> SEQUENCE: 46

```
gctcgagact acaaagacca tgacggtgat tataaagatc atgacatcga ctacaaggat      60
gacgatgaca agggtcatca tcaccatcac cattga                               96
```

<210> SEQ ID NO 47
<211> LENGTH: 26
<212> TYPE: PRT
<213> ORGANISM: Homo sapiens

<400> SEQUENCE: 47

```
Met Tyr Ser Ala Pro Ser Ala Cys Thr Cys Leu Cys Leu His Phe Leu
1               5                   10                  15

Leu Leu Cys Phe Gln Val Gln Val Leu Val
            20                  25
```

<210> SEQ ID NO 48
<211> LENGTH: 78
<212> TYPE: DNA
<213> ORGANISM: Homo sapiens

<400> SEQUENCE: 48

```
atgtattcag cgccctccgc ctgcacttgc ctgtgtttac acttcctgct gctgtgcttc      60
caggtacagg tgctggtt                                                   78
```

<210> SEQ ID NO 49
<211> LENGTH: 26
<212> TYPE: PRT
<213> ORGANISM: Mus musculus

<400> SEQUENCE: 49

```
Met Tyr Ser Ala Pro Ser Ala Cys Thr Cys Leu Cys Leu His Phe Leu
1               5                   10                  15

Leu Leu Cys Phe Gln Val Gln Val Leu Ala
            20                  25
```

-continued

<210> SEQ ID NO 50
<211> LENGTH: 78
<212> TYPE: DNA
<213> ORGANISM: Mus musculus

<400> SEQUENCE: 50
atgtattcag cgccctccgc ctgcacttgc ctgtgtttac actttctact gctgtgcttc    60
caggttcagg tgttggca                                                  78

<210> SEQ ID NO 51
<211> LENGTH: 34
<212> TYPE: DNA
<213> ORGANISM: Artificial
<220> FEATURE:
<223> OTHER INFORMATION: Primer

<400> SEQUENCE: 51
atgtattcag cgccctccgc ctgcacttgc ctgt                                34

<210> SEQ ID NO 52
<211> LENGTH: 34
<212> TYPE: DNA
<213> ORGANISM: Artificial
<220> FEATURE:
<223> OTHER INFORMATION: Primer

<400> SEQUENCE: 52
ctagccgggg tgagtggggc ggatccgccg ggat                                34

<210> SEQ ID NO 53
<211> LENGTH: 13
<212> TYPE: DNA
<213> ORGANISM: Artificial
<220> FEATURE:
<223> OTHER INFORMATION: Primer

<400> SEQUENCE: 53
cagccgctcg aga                                                       13

<210> SEQ ID NO 54
<211> LENGTH: 13
<212> TYPE: DNA
<213> ORGANISM: Artificial
<220> FEATURE:
<223> OTHER INFORMATION: Primer

<400> SEQUENCE: 54
tgcgggccct caa                                                       13

<210> SEQ ID NO 55
<211> LENGTH: 59
<212> TYPE: DNA
<213> ORGANISM: Artificial
<220> FEATURE:
<223> OTHER INFORMATION: Primer

<400> SEQUENCE: 55
ccgctcgaga ctacaaagac catgacggtg attataaaga tcatgacatc gactacaag     59

<210> SEQ ID NO 56
<211> LENGTH: 59
<212> TYPE: DNA
<213> ORGANISM: Artificial
<220> FEATURE:

<223> OTHER INFORMATION: Primer

<400> SEQUENCE: 56
tgcgggccct caatggtgat ggtgatgatg acccttgtca tcgtcatcct tgtagtcga        59

<210> SEQ ID NO 57
<211> LENGTH: 38
<212> TYPE: DNA
<213> ORGANISM: Artificial
<220> FEATURE:
<223> OTHER INFORMATION: Primer

<400> SEQUENCE: 57
gtgaatgcca tatggccgag gagaatgtgg acttccgc        38

<210> SEQ ID NO 58
<211> LENGTH: 38
<212> TYPE: DNA
<213> ORGANISM: Artificial
<220> FEATURE:
<223> OTHER INFORMATION: Primer

<400> SEQUENCE: 58
gtgaatgcca tatggtggac ttccgcatcc acgtggag        38

<210> SEQ ID NO 59
<211> LENGTH: 38
<212> TYPE: DNA
<213> ORGANISM: Artificial
<220> FEATURE:
<223> OTHER INFORMATION: Primer

<400> SEQUENCE: 59
gtgaatgcca tatgaaccag acgcgggctc gagatgat        38

<210> SEQ ID NO 60
<211> LENGTH: 38
<212> TYPE: DNA
<213> ORGANISM: Artificial
<220> FEATURE:
<223> OTHER INFORMATION: Primer

<400> SEQUENCE: 60
gtgaatgcca tatggctcga gatgatgtga gtcggaag        38

<210> SEQ ID NO 61
<211> LENGTH: 38
<212> TYPE: DNA
<213> ORGANISM: Artificial
<220> FEATURE:
<223> OTHER INFORMATION: Primer

<400> SEQUENCE: 61
gtgaatgcca tatggatgat gtgagtcgga agcagctg        38

<210> SEQ ID NO 62
<211> LENGTH: 38
<212> TYPE: DNA
<213> ORGANISM: Artificial
<220> FEATURE:
<223> OTHER INFORMATION: Primer

<400> SEQUENCE: 62
gtgaatgcca tatgcggaag cagctgcgct tgtaccag        38

<210> SEQ ID NO 63
<211> LENGTH: 38
<212> TYPE: DNA
<213> ORGANISM: Artificial
<220> FEATURE:
<223> OTHER INFORMATION: Primer

<400> SEQUENCE: 63
gtgaatgcca tatgaagcac attcaagtcc tgggccgt                              38

<210> SEQ ID NO 64
<211> LENGTH: 38
<212> TYPE: DNA
<213> ORGANISM: Artificial
<220> FEATURE:
<223> OTHER INFORMATION: Primer

<400> SEQUENCE: 64
gtgaatgcca tatggcccgt ggcgaggacg gggacaag                              38

<210> SEQ ID NO 65
<211> LENGTH: 38
<212> TYPE: DNA
<213> ORGANISM: Artificial
<220> FEATURE:
<223> OTHER INFORMATION: Primer

<400> SEQUENCE: 65
gtgaatgcca tatggggagt caagtccgga tcaagggc                              38

<210> SEQ ID NO 66
<211> LENGTH: 38
<212> TYPE: DNA
<213> ORGANISM: Artificial
<220> FEATURE:
<223> OTHER INFORMATION: Primer

<400> SEQUENCE: 66
gtgaatgcca tatgacagaa ttctacctgt gtatgaac                              38

<210> SEQ ID NO 67
<211> LENGTH: 38
<212> TYPE: DNA
<213> ORGANISM: Artificial
<220> FEATURE:
<223> OTHER INFORMATION: Primer

<400> SEQUENCE: 67
gtgaatgcca tatgggtact agcaaggagt gcgtgttc                              38

<210> SEQ ID NO 68
<211> LENGTH: 34
<212> TYPE: DNA
<213> ORGANISM: Artificial
<220> FEATURE:
<223> OTHER INFORMATION: Primer

<400> SEQUENCE: 68
gaagatctct tcaatggtga tggtgatgat gacc                                  34

<210> SEQ ID NO 69
<211> LENGTH: 34
<212> TYPE: DNA
<213> ORGANISM: Artificial
<220> FEATURE:
<223> OTHER INFORMATION: Primer -continued

```
<400> SEQUENCE: 69
atgtattcag cgccctccgc ctgcacttgc ctgt                                34

<210> SEQ ID NO 70
<211> LENGTH: 34
<212> TYPE: DNA
<213> ORGANISM: Artificial
<220> FEATURE:
<223> OTHER INFORMATION: Primer

<400> SEQUENCE: 70
ctaggcaggg tgtgtgggcc ggatccgacg ggac                                34

<210> SEQ ID NO 71
<211> LENGTH: 38
<212> TYPE: DNA
<213> ORGANISM: Artificial
<220> FEATURE:
<223> OTHER INFORMATION: Primer

<400> SEQUENCE: 71
gtgaatgcca tatgaaacac atccaggtcc tgggccgc                            38
```

ISOLATED MUTANT PROTEIN OF FIBROBLAST GROWTH FACTOR 18 AND PHARMACEUTICAL COMPOSITION COMPRISING THE SAME

FIELD OF THE INVENTION

The present invention relates to mutant growth factor proteins having altered receptor specificities, which are produced by deleting appropriate numbers of amino acid residues from the N-terminus of fibroblast growth factor 18 (FGF18) protein. The present invention also relates to a pharmaceutical composition comprising the mutant growth factor protein as an active ingredient.

BACKGROUND ART

Heretofore, it is known that the fibroblast growth factor (FGF) ligand family comprises 22 members in humans and mice, and that each of these members has an inherent reaction specificity for one or more of seven FGF receptor (FGFR) subclasses, namely FGFR1c, FGFR1b, FGFR2c, FGFR2b, FGFR3c, FGFR3b and FGFR4. It is generally believed that the diversity of the physiological functions of FGF ligands is often explainable in terms of the combinations of various ligands and various receptors. On the other hand, few cases are known in which the inherent receptor specificities of the individual FGF ligands can be regulated artificially.

Under these circumstances, it has been reported that FGF18 can regulate the formation or growth of a bone or cartilage (Non-patent References Nos. 1 and 2). It has been also reported that FGF18 can induce the anagen phase of hair follicles to stimulate the growth of hair (Non-patent Reference No. 3). However, it is not clear which of the FGF receptors binds and reacts with FGF18 to enable it to exhibit those and various other physiological activities of the FGF18. If the receptor specificity of naturally secreted FGF18 can be manipulated, then a factor which specifically exhibits or regulates any one of the various activities of FGF18 might be found. However, no such factors have been discovered yet. It is believed that naturally secreted FGF18 reacts with FGFR1c, FGFR2c, FGFR3c or FGFR4.

Heretofore, no mutant FGF18 proteins having different reaction specificities to FGF18 receptors have been known, and no mutant FGF18 proteins capable of regulating the activity of naturally secreted FGF18 have been known, either. Those mutant FGF18 proteins would be highly valuable, since FGF18 has an activity as a regulation factor for the hair growth, an activity as a regulation factor for the formation, growth or repairment of a bone or cartilage, and many other activities.

[Non-Patent Reference No. 1]
Ohbayashi N, Shibayama M, Kurotaki Y, Imanishi M, Fujimori T, Itch N, Takada S. FGF18 is required for normal cell proliferation and differentiation during osteogenesis and chondrogenesis. Genes Dev. 2002, 16(7):870-9

[Non-Patent Reference No. 2]
Moore E E, Bendele A M, Thompson D L, Littau A, Waggie K S, Reardon B, Ellsworth J L. Fibroblast growth factor-18 stimulates chondrogenesis and cartilage repair in a rat model of injury-induced osteoarthritis. Osteoarthritis Cartilage. 2005, 13(7):623-31

[Non-Patent Reference No. 3]
Kawano N, Komi-Kuramochi A, Asada M, Suzuki M, Oki J, Jiang J, Imamura T. Comprehensive analysis of FGF and FGFR expression in skin: FGF18 is highly expressed in hair follicles and capable of inducing anagen from telogen stage hair follicles. J Invest Dermatol. 2005, 124(5):877-885

DISCLOSURE OF THE INVENTION

Problems to be Solved by the Invention

While there are seven FGF receptor subclasses (FGFR1c, FGFR1b, FGFR2c, FGFR2b, FGFR3c, FGFR3b and FGFR4), FGF18 is believed to react with at least four of them, namely, FGF1c, FGFR2c, FGFR3c and FGFR4. The activity of FGF18 manifests itself in different ways depending on the type or amount of the receptor expressed by a target cell or the nature of the target cell, and functions to regulate a wide variety of life processes including the formation or growth of a bone or cartilage, the formation of lung and the growth of hair. Therefore, if it is desired to regulate any one of the life processes selectively, a protein having the desired receptor specificity but having no undesired receptor specificity would be useful.

Thus, the present invention aims to provide a mutant FGF18 protein having a different receptor specificity from the reaction specificity that a naturally secreted FGF18 has for its receptor.

Means for Solving the Problems

The present inventors have made intensive and extensive studies for solving the above-mentioned problems. As a consequence, the present inventors have succeeded in producing mutant FGF18 proteins having different receptor specificities from the reaction specificity that naturally secreted FGF18 is known to have for its receptor. For example, a mutant FGF18 protein can be produced which does not react with the FGF receptor subclass FGFR1c but reacts specifically with FGFR4. A mutant FGF18 protein can also be produced which does not react with the FGF receptor subclass FGFR1c or FGFR4 but reacts specifically with FGFR2b. These proteins can induce and regulate only part of life processes induced by naturally secreted FGF1S, and therefore can be used as medicinal agents. Based on these findings, the present invention has been accomplished.

The summary of the invention is as follows.

(1) A protein selected from the following proteins (a) to (d):

(a) a mutant protein of naturally secreted fibroblast growth factor 18, which comprises an amino acid sequence having the one or more amino acid residues deleted from the N-terminus of the amino acid sequence of naturally secreted fibroblast growth factor 18 so as to have an altered fibroblast growth factor receptor specificity;

(b) a protein which comprises an amino acid sequence having one or several amino acid residues deleted, substituted or added in the amino acid sequence of the mutant protein (a) and which has an altered fibroblast growth factor receptor specificity compared to naturally secreted fibroblast growth factor 18;

(c) the protein (a) or (b) having the addition of a secretion signal sequence and/or a tag sequence; and (d) the protein (a), (b) or (c) having any modification that has no influence on the functions thereof.

(2) The protein according to item (1) wherein the mutant protein (a) comprises an amino acid sequence depicted in any one of SEQ ID NOs:2 to 11 or 13 to 22.

(3) The protein according to item (2), wherein the mutant protein (a) is encoded by a DNA sequence depicted in any one of SEQ TD NOs:24 to 33 or 35 to 44.

(4) The protein according to any one of items (1) to (3), wherein the mutant protein (a) comprises an amino acid sequence having 4 to 22 amino acid residues other than methionine deleted from the N-terminus of the amino acid sequence of naturally secreted fibroblast growth factor 18.

(5) A pharmaceutical composition comprising a protein as recited in any one of items (1) to (4).

(6) The pharmaceutical composition according to item (5) for reacting with a product of gene 4 of a fibroblast growth factor receptor to regulate a cellular function.

(7) The pharmaceutical composition according to item (5) for the regulation of hair regeneration or hair growth.

(8) The pharmaceutical composition according to item (5) for the regulation of bone or cartilage formation.

(9) A method for producing a mutant protein having an altered fibroblast growth factor receptor specificity, which comprises deleting one or more amino acid residues from the N-terminus of the amino acid sequence of naturally secreted fibroblast growth factor 18.

The present invention provides a mutant FGF18 protein which has a different receptor specificity from the reaction specificity that naturally secreted FGF18 protein has for its receptor.

The present invention also provides a pharmaceutical composition which is effective for positively or negatively regulating a physiological activity of FGF18. Specifically, a pharmaceutical composition is provided which has an activity similar to that of FGF18 in regulating the hair regeneration or growth (which is a part of the hair production mechanism) or an activity of specifically inhibiting that activity, but does not have any other, undesirable physiological activity of FGF18, and which is therefore effective for the regulation of hair regeneration or growth. A pharmaceutical composition is also provided which has an activity similar to that of FGF18 in promoting the bone formation or inhibiting the cartilage formation or a specific inhibition activity on those activities of FGF18, but does not have any other, undesired physiological activity of FGF18, and which is therefore effective for the regulation of bone or cartilage formation.

The present invention further provides a pharmaceutical composition effective for the inhibition of neuronal cell death or the regulation of the expression of other FGF groups, a composition effective for various types of regenerative medicine, and the like.

EFFECT OF THE INVENTION

The novel mutant FGF18 proteins according to the present invention have different receptor specificities from the reaction specificity that naturally secreted FGF18 has for its receptor. This makes it becomes possible to regulate a physiological activity of FGF18 positively or negatively.

BEST MODE FOR CARRYING OUT THE INVENTION

Figure 1:
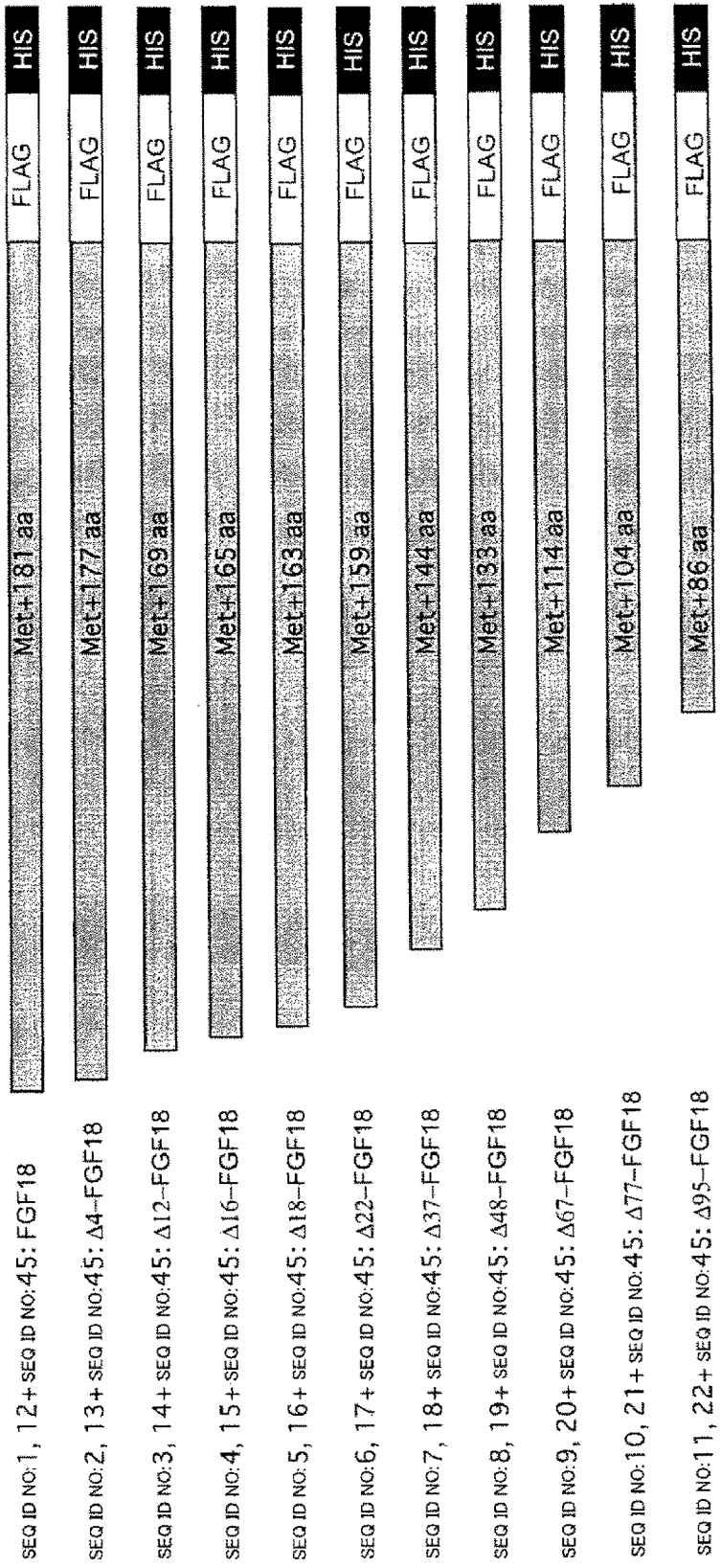
FIG. 1 schematically illustrates the structures of mutant FGF18 proteins which were analyzed in Examples of the present invention.

Hereinbelow, the present invention will be described in detail.

Each of the mutant growth factor proteins according to the present invention is a protein which comprises an amino acid sequence having an appropriate length shortened from the N-terminus of FGF18 protein.

In both of humans and mice, FGF18 protein is synthesized as a polypeptide of 207 amino acid residues in the cytoplasm of an FGF18-protein-producing cell. Upon the secretion of FGF18 protein out of the cell, a signal peptide located at the N-terminus thereof is cleaved out. The term "naturally secreted FGF18" as used herein refers to a protein comprising a full-length amino acid sequence as a secreted form of FGF18 which is composed of 181 amino acid residues and has a methionine residue for initiation of translation attached to the amino terminus thereof to make a total of 182 amino acid residues as exemplified by a protein comprising the amino acid sequence depicted in SEQ ID NO:1 or a protein comprising the amino acid sequence depicted in SEQ ID NO:12. In contrast, it has been demonstrated in the present invention that a mutant protein having 4, 12, 16, 18, 22, 37, 48, 67, 77 or 95 amino acid residues deleted from the amino terminus excluding methionine is an activated mutant growth factor protein having an altered receptor specificity. It might be theorized that a polypeptide comprising a sequence starting from the third amino acid residue in the sequence depicted in SEQ ID NO:1 is the naturally secreted form of FGF18 protein. However, the addition of the second amino acid residue in the sequence depicted in SEQ ID NO:1 will not cause any difference in the activity of the polypeptide.

Specifically, the mutant growth factor protein of the present invention is a protein substantially comprising an amino acid sequence depicted in any one of SEQ ID NOs:2 to 11 for human, or is a protein substantially comprising an amino acid sequence depicted in any one of SEQ ID NOs:13 to 22 for a mouse; the former protein is encoded by a DNA sequence depicted in any one of SEQ ID NOs:24 to 33 and the latter protein is encoded by a DNA sequence depicted in any one of SEQ ID NOs:35 to 44. The term "substantially" as used herein means that the amino acid sequences may in part have an addition, deletion, substitution or modification as long as the resulting amino acid sequence can exhibit its functions.

The mutant growth factor proteins of the present invention further include a protein substantially having a deletion of up to 22 amino acid residues from the amino terminus of the protein depicted in SEQ ID NO:1 or 12.

The mutant growth factor proteins of the present invention further include any one of the proteins which are primarily defined by cDNA sequences depicted in the Sequence Listing, and also include a modified form of protein which has a peptide sequence added at the amino terminus thereof as a so-called signal peptide that is required for its secretion from an animal cell or the like. Also included is a modified form of protein which has a methionine residue for the initiation of translation added thereto, in order to produce the mutant growth factor protein in an *E. coli* cell in a form having no signal peptide. Further, included are a modified form of protein which has a tag for detection or purification added to the N- or C-terminus thereof, as well as a modified form of protein with a modification having no influence on the functions of the resulting mutant growth factor protein. Examples of the tag for detection or purification include FLAG-His tag, His tag, FLAG tag, c-Myc tag, HA tag, V5 tag, GFP tag and combinations thereof. Examples of the modification having no influence on the function of the protein include modifications which naturally occur in the production system such as methylation of the N-terminal amino acid residue, addition of a sugar chain and phosphorylation, and modifications involving techniques such as the addition of polyethylene glycol that have already been established for application to other proteins.

In other words, the mutant growth factor protein that is to be added to the pharmaceutical composition of the present invention as an active ingredient in the form of a recombinant or the like retains its usefulness even if it is produced in those forms.

Hereinbelow, the method for preparing the mutant growth factor protein of the present invention will be described in detail.

First, RNA extracted from an animal tissue is reverse transcribed using a random hexaoligonucleotide as a primer, and the product is amplified by PCR. In this procedure, a DNA fragment having a size corresponding to that of known FGF18 protein can be produced by using an oligonucleotide capable of amplifying an FGF18 open reading frame as the primer. The resulting DNA fragment is separated by gel electrophoresis, cleaved from the gel, and integrated into a cloning vector at a multi-cloning site to produce a plasmid.

With the thus produced FGF18 cDNA carrying plasmid used as a template and with a variety of oligonucleotides designed to encode the naturally secreted FGF18 and proteins having a deletion at its N-terminus being used as primers, PCR reaction is performed to produce DNA fragments that correspond to the respective proteins in size. The DNA fragments are separated by gel electrophoresis, cleaved from the gel, and integrated into a cloning vector at a multi-cloning site, thereby producing a plasmid. In the designing of the oligonucleotides, the number of amino acid residues to be deleted from the N-terminus can be determined arbitrarily, and a sequence encoding the substitution, addition or deletion of an amino acid residue may be contained in the sequence of each oligonucleotide. By designing as mentioned above, DNA fragments each encoding an amino acid sequence having one or several amino acid residues deleted, substituted or added in the amino acid sequence of the protein mutant. The DNA fragments are separated by gel electrophoresis, cleaved from the gel, and integrated into a cloning vector at a multi-cloning site to produce a plasmid.

The plasmid into which DNA is to be inserted may be of any type as long as it can be replicated and maintained in a host cell. Examples of the plasmid include pBR322 and pUC18 which are derived from *E. coli*, and pET-3c which is constructed based on pBR322 and pUC18.

The method for integrating into a plasmid may be a method disclosed in T. Maniatis et al., Molecular Cloning, Cold Spring Harbor Laboratory, p. 239 (1982) or the like.

The cloned gene can be linked downstream of a promoter in a vector suitable for the expression of the gene, thereby producing an expression vector. The vector may be a plasmid derived from *E. coli* as mentioned above (e.g., pBR322, pBR325, pUC12, pUC13, pET-3), a plasmid derived from *Bacillus subtilis* (e.g., pUB110, pTP5, pC194), a plasmid derived from yeast (pSH19, pSH15), a bacteriophage (e.g., λ-phage) or a derivative thereof, an animal virus (e.g., retrovirus, vaccinia virus), an insect virus or the like.

The gene may have an ATG sequence at the 5'-terminus as the translation initiation codon, and it may have a TAA sequence, a TGA sequence or a TAG sequence as the translation termination codon at the 3'-terminus. Alternatively, the gene may have a DNA sequence encoding a tag sequence at the 3'-terminus in place of the translation termination codon. For the expression of the gene, a promoter is linked upstream of the gene. The promoter to be used in the present invention may be of any type, as long as it is applicable to the host employed for the expression of the gene.

When an *E. coli* cell is used as the host to be transformed, it is preferred to use trp promoter, lac promoter, rec A promoter, λPL promoter, lpp promoter, T7 promoter or the like. When the host is a *Bacillus subtilis* cell, it is preferred to use SP01 promoter, SP02 promoter, penP promoter or the like. When the host is a yeast cell, it is preferred to use PHO5 promoter, PGK promoter, GAP promoter, ADH promoter or the like. When the host is an animal cell, it is preferred to use a promoter derived from SV40 or a promoter for a retrovirus.

As for the tag sequence, its nucleotide sequence can be synthesized based on the known information about its sequence.

The thus constructed vector carrying recombinant DNA having a nucleotide sequence encoding a mutant growth factor protein can be used to produce a transformant carrying the vector.

Examples of the host that can be used include an *E. coli* cell (e.g., BL21, BL21(DE3), BL21(DE3)pLysS, BL21(DE3)pLysE), a *Bacillus subtilis* cell (e.g., *Bacillus subtilis* DB105), a yeast cell (e.g., *Pichia pastoris*, *Saccharomyces cerevisiae*), an animal cell (e.g., COS cell, CHO cell, BHK cell, NIH3T3 cell, BALB/c3T3 cell, HUVE cell, LEII cell), and an insect cell.

The transformation can be achieved by a method conventionally employed for a host. Alternatively, any unconventional method may be used as long as it is applicable to the host employed. For example, when the host is an *E. coli* cell, a vector carrying the recombinant DNA is introduced by the temperature shock method or electroporation into a competent cell prepared by the calcium method or the like. When the host is a yeast cell, a vector carrying the recombinant DNA is Introduced by the temperature shock method or electroporation into a competent cell prepared by the lithium method or the like. When the host is an animal cell, a vector carrying the recombinant DNA is introduced into a cell in the growth phase by the calcium phosphate method, the lipofection method or the electroporation method.

The transformant produced in this manner is cultured to produce the mutant growth factor protein.

In the culture of the transformant, a culture medium to be used is one which is conventionally used for the culture of the host employed. Alternatively, an unconventional culture medium may be used as long as it is applicable to the host employed. For example, when the host is an *E. coli* cell, an LB medium or the like is used. When a yeast cell is used as the host, an YPD medium or the like is used. When an animal cell is used as the host, Dulbecco's MEM supplemented with an animal serum or the like is used. The culture is carried out under conditions which are conventionally used for the host employed. Alternatively, unconventional culture conditions may be used as long as they are applicable to the host employed. For example, when the host is an *E. coli* cell, the culture is carried out at about 30 to 37° C. for about 3 to 24 hours with optional aeration or agitation. When the host is a yeast cell, the culture is carried out at about 25 to 37° C. for about 12 hours to 2 weeks with optional aeration or agitation. When the host is an animal cell, the culture is carried out at about 32 to 37° C. under the conditions of 5% $CO_2$ and 100% humidity for about 24 hours to 2 weeks with optional variation in gas phase conditions or addition of agitation.

For extracting the mutant growth factor protein from the cultured cell contained in the culture, the cultured cell is disrupted with a homogenizer, a French press, an ultrasonic wave, lysozyme and/or a freeze-thawing process to cause the desired protein to elute from the cell. The desired protein can be obtained from a soluble fraction. If the desired protein is contained in an insoluble fraction, it is possible to employ a procedure comprising disrupting the cell, collecting the insoluble fraction by centrifugation, and rendering the insoluble fraction soluble with a buffer solution containing guanidine hydrochloride or the like. Alternatively, the cell may be disrupted directly with a buffer solution containing a protein-denaturing agent such as guanidine hydrochloride to elute the desired protein from the cell.

The purification of the mutant growth factor protein from the supernatant can be achieved by any appropriate combination of known separation/purification methods. The known separation/purification methods that may be employed include salting-out, solvent precipitation, dialysis, ultrafiltration, gel filtration, SDS-polyacrylamide gel electrophoresis, ion exchange chromatography, affinity chromatography, reverse-phase high performance liquid chromatography, isoelectric focusing and the like. For many mutant growth factor proteins, the affinity chromatography method using heparin sepharose as the carrier may be applied. For purification of a protein with a tag added thereto, known separation/purification methods effective for the tag may be employed in any appropriate combination.

The sample produced in this manner may be dialyzed and lyophilized to produce a dried powder, as long as the activities of the mutant growth factor protein contained in the sample are not impaired. The sample may be added with a carrier such as serum albumin for storage. This is effective for preventing the mutant protein in the sample from being adsorbed onto the wall of its container during storage.

The sample may be added with a trace amount of a reducing agent during the purification process or the storage process. This is effective for preventing the oxidation of the sample. Examples of the reducing agent include β-mercaptoethanol, dithiothreitol and glutathione.

The mutant growth factor proteins according to the present invention include one having an activity of activating FGFR4 specifically among FGF receptors.

The mutant growth factor proteins according to the present invention include one having an action for activating FGFR1c among FGF receptors.

The mutant growth factor proteins according to the present invention include one having an action for activating FGFR2b weakly among FGF receptors.

The mutant growth factor proteins according to the present invention include one having an action for exhibiting or regulating at least a part of the physiological functions of FGF18.

The physiological functions of FGF18 include an action for regulating the hair growth mechanism, specifically an action for promoting or inhibiting the regeneration of hair on the head or the like, or an action for promoting or inhibiting the growth of hair.

The physiological functions of FGF18 also include an action for regulating the mechanism of the formation or growth of a bone or a cartilage, specifically an action for promoting or inhibiting the formation of a bone or a cartilage.

The mutant growth factor protein according to the present invention also has an action for regulating other physiological functions of FGF18.

The other physiological functions of FGF18 include regulation of lung formation, promotion or inhibition of the growth or differentiation of fibroblasts, vascular endothelial cells, myoblasts, neuronal cells or glia cells, and regulation of the functions of these cells or inhibition of the death of these cells.

The mutant growth factor protein according to the present invention can react with a product of gene-4 of a fibroblast growth factor receptor to regulate a cellular function. The product of gene-4 of a fibroblast growth factor receptor may have a variety of modifications including various types of splicing during the production of mature mRNA and addition of a sugar chain after translation.

The mutant growth factor protein produced in the above-mentioned manner can be prepared into pharmaceutical compositions in the form of a liquid, a lotion, an aerosol, an injection, a powder, a granule, a tablet, a suppository, an enteric coated tablet or a capsule by conventional methods known for the production of drug preparations using pharmaceutically acceptable solvents, excipients, carriers, auxiliary agents or the like.

The content of the mutant growth factor protein in the pharmaceutical composition as an active ingredient may be approximately 0.0000000001 to 1.0% by weight.

The pharmaceutical composition can be safely administered to a mammal (e.g., human, a mouser a rat, a rabbit, a dog, a cat) parenterally or orally as a hair regeneration-promoting agent, a hair growth agent, a bone formation promoter, a cartilage formation inhibitor, a nutrient/function-regulator for the brain-nervous system, a learning effect regulator or the like. The dose amount of the pharmaceutical composition may vary depending on the type of the dosage form, the route of administration, the condition of the subject under treatment or the like. Consider, for example, the case of administration to a mammal including human; the mutant growth factor protein can be applied to the affected part in several divided doses of 0.0001 to 1000 mg in total per day.

EXAMPLES

Hereinafter, the present invention will be described in great detail with reference to the following examples, to which the present invention is by no means limited.

(1) Construction of Plasmids

Construction of Plasmids Carrying cDNAs Encoding Mouse Mutant FGF18 Proteins cDNA molecules encoding mouse mutant FGF18 proteins can be produced as follows.

As the material for the production, a piece of skin was removed from a 7-week-old male C3H/HeN mouse (Japan SLC, Hamamatsu, Japan), and RNA was extracted from the skin. One microgram of the mouse RNA was added with 120 ng of random hexanucleotide DNA (GIBCO BRL, Tokyo, Japan). By using 200 units of M-HLV reverse transcriptase (GIBCO BRL, Tokyo, Japan), a cDNA mixture was prepared.

From the cDNA mixture, cDNA encoding mouse full-length FGF18 was amplified by PCR. The sequences of the primers used in the PCR are as follows.

```
Sense primer:
                                      (SEQ ID NO: 51)
5'-ATGTATTCAGCGCCCTCCGCCTGCACTTGCCTGT-3'

Anti-sense primer:
                                      (SEQ ID NO: 52)
5'-CTAGCCGGGGTGAGTGGGGCGGATCCGCCGGGAT-3'
```

To produce cDNA encoding a tag comprising three FLAG tag sequences made continuously integral with a His tag sequence (the tag is hereinafter referred to as "FLAG-His tag"), PCR was carried out using primers #468 (5'-CAG CCG CTC GAG A-S' (SEQ ID NO:53)) and #469 (5'-TGC GGG CCC TCAA-3' (SEQ ID NO:54)) in the presence of megaprimers #466 (5'-CCG CTC GAG ACT ACA AAG ACC ATG ACG GTG ATT ATA AAG ATC ATG ACA TCG ACT ACA AG-3' (SEQ ID NO:55)) and #467 (5'-TGC GGG CCC TCA ATG GTG ATG GTG ATG ATG ACC CTT GTC ATC GTC ATC CTT GTA GTC GA-3' (SEQ ID NO:56)) as templates. The reaction product was digested with Xho I and Apa I, and cloned into preliminarily digested pcDNAΔ3.1(+) (Invitrogen Corp), thereby producing a plasmid FLAG-His/pcDNAΔ3.1(+). The plasmid FLAG-His/pcDNAΔ3.1(+) was amplified by PCR using two primers, one comprising a sequence homologous to the 5'-terminus of FGF18 ORF and carrying an EcoRV-recognizing sequence and the other comprising a sequence homologous to the 3'-terminus of FGF18 ORF and carrying a SalI-recognizing sequence, with FGF18 ORF being used as a template. The resulting product was digested with EcoRV and SalI, inserted into FLAG-His/pcDNAΔ3.1(+) preliminarily digested with EcoRV and XhoI, thereby producing cDNA encoding FGF18 protein having a FLAG-His tag linked thereto. The nucleotide sequence of the cDNA was confirmed to be a sequence that was completely identical to the sequence depicted in SEQ ID NO:34 except the first ATG.

Next, a cDNA molecule for naturally secreted FGF18 depicted in SEQ ID NO:34 and cDNA molecules for FGF18 mutants depicted in SEQ ID NOs:35 to 44 were produced by PCR using the mouse full-length FGF18 cDNA as a template. Each of the cDNA molecules was cloned into a vector, and the sequence of the product was confirmed. The sequences of the primers used in the PCR are as follows.

```
Sense primers
#Full-length (38bp):
                                        (SEQ ID NO: 57)
    5'-GTGAATGCCATATGgccgaggagaatgtggacttccgc-3';

#226 (38bp):
                                        (SEQ ID NO: 58)
    5'-GTGAATCCCATATGGTGGACTTCCGCATCCACGTGGAG-3';

#249 (38bp):
                                        (SEQ ID NO: 59)
    5'-GTGAATGCCATATGAACCAGACGCGGGCTCGAGATGAT-3';

#262 (38bp):
                                        (SEQ ID NO: 60)
    5'-GTGAATGCCATATGGCTCGAGATGATGTGAGTCGGAAG-3';

#268 (38bp):
                                        (SEQ ID NO: 61)
    5'-GTGAATGCCATATGGATGATGTGAGTCGGAAGCAGCTG-3';

#280 (38bp):
                                        (SEQ ID NO: 62)
    5'-GTGAATGCCATATGCGGAAGCAGCTGCGCTTGTACCAG-3';

#325 (38bp):
                                        (SEQ ID NO: 63)
    5'-GTGAATGCCATATGAAGCACATTCAAGTCCTGGGCCGT-3';

#358 (38bp):
                                        (SEQ ID NO: 64)
    5'-GTGAATGCCATATGGCCCGTGGCGAGGACGGGGACAAG-3';

#415 (38bp):
                                        (SEQ ID NO: 65)
    5'-GTGAATGCCATATGGGGAGTCAAGTCCGGATCAAGGGC-3';

#445 (38bp):
                                        (SEQ ID NO: 66)
    5'-GTGAATGCCATATGACAGAATTCTACCTGTGTATGAAC-3';

#498 (38bp):
                                        (SEQ ID NO: 67)
    5'-GTGAATGCCATATGGGTACTAGCAAGGAGTGCGTGTTC-3';

Anti-sense primer
#537 (34bp):
                                        (SEQ ID NO: 68)
    5'-GAAGATCTCTTCAATGGTGATGGTGATGATGACC-3'
```

The cDNA sequences depicted in SEQ ID NOs:34 to 44 are each designated with a translation termination codon tag attached thereto. In the actually produced constructs, however, this tag is not included since a tag sequence follows the FGF18 sequence (after the C-terminus).

Acquisition of cDNAs Encoding Human Mutant FGF18 Proteins

Molecules of cDNA that encode human mutant FGF18 proteins can be readily acquired in basically the same manner as mouse mutant FGF18 proteins.

As the material for production, human RNA such as "Human Brain Whole RNA" available from Clontech Laboratories, Inc. (Catalog number 64020-1) was used. One microgram of this human RNA was added with 120 ng of random hexanucleotide DNA, and a cDNA mixture was prepared by using 200 units of M-HLV reverse transcriptase.

From the cDNA mixture, cDNA encoding the human full-length FGF18 was amplified by PCR. The cDNA was cloned into a pBlueScript vector. The nucleotide sequence of the cDNA was confirmed to be a sequence that was completely identical to the sequence depicted in SEQ ID NO:23 except the first ATG. The primers used in the PCR are as follows.

```
Sense primer:
                                        (SEQ ID NO: 69)
    5'-atgtattcagcgccctccgcctgcacttgcctgt-3';

Antisense primer:
                                        (SEQ ID NO: 70)
    5'-caggcagggtgtgtgggccggatccgacgggac-3'
```

Subsequently, a cDNA molecule for the naturally secreted FGF18 depicted in SEQ ID NO:23 and cDNA molecules for the mutant FGF18 proteins depicted in SEQ ID NOs:24 to 33 were produced by PCR using the human full-length FGF18 cDNA as a template. Each of the cDNA molecules was cloned into a vector, and the sequence was confirmed. In this experiment, the same primers as in the experiment for the production of cDNAs encoding mouse mutant FGF18 proteins were used, except for #325 (38 bp). In the production of cDNAs encoding human mutant FGF18 proteins, a primer 5'-GTGAATGCCATATGAAACACATCCAGGTC-CTGGGCCGC-3' (SEQ ID NO: 71) (38 bp) was used in place of #325 (38 bp).

The cDNA sequences depicted in SEQ ID NOs:23 to 33 are each designated with a translation termination codon tag attached thereto. In the actually produced constructs, however, this tag is not included since a tag sequence follows the FGF18 sequence (after the C-terminus)

(2) Expression and Identification of Mutant FGF18 Proteins

Figure 2:
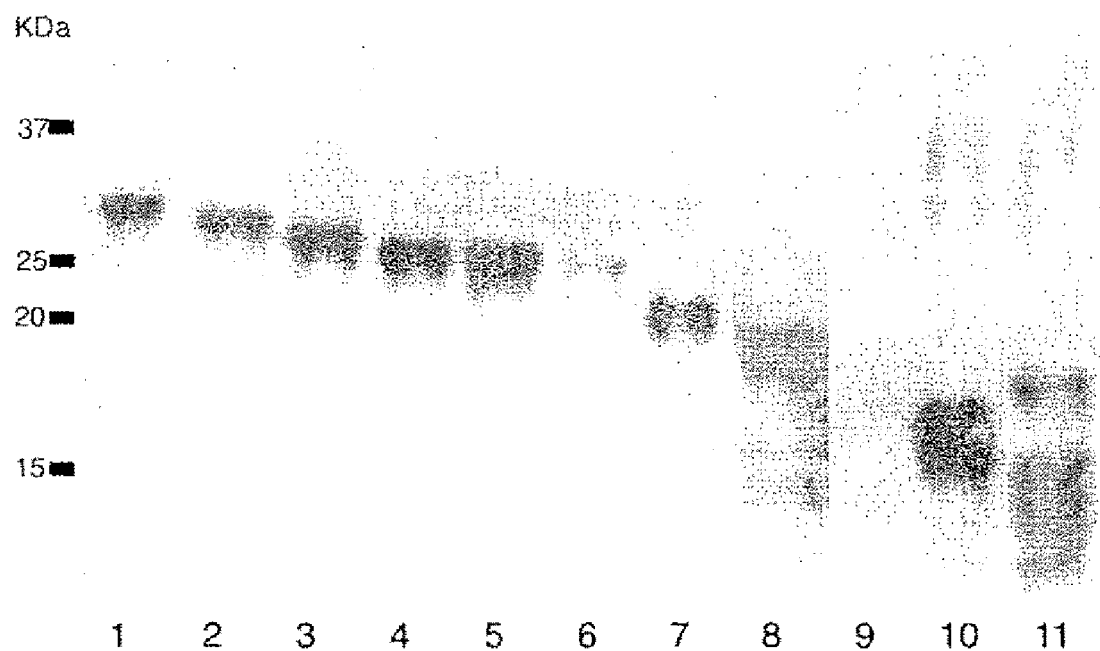
FIG. 2 shows the results of detection by western blotting of mutant FGF18 proteins which were expressed in an *E. coli* expression system and purified.

A plasmid was prepared by adding the cDNA encoding a FLAG-His tag (mentioned above) to the 3'-terminus of each of the mouse mutant FGF18 proteins and inserting the resulting sequence downstream of T7 promoter of pET-3c vector (Takara Bio Inc.). *E. coli* BL21(DE3)pLysS (Takara Bio Inc.) was transformed in a conventional manner by using the plasmid, and a protein was produced in the *E. coli* cell. The *E. coli* cell was disrupted to produce a water-soluble fraction. The mutant FGF18 protein was purified from the water-soluble fraction by chromatography on a nickel column in accordance with a conventional His-tagged protein purification method. The purified protein was separated by SDS-polyacrylamide gel electrophoresis, and then transferred onto a nitrocellulose membrane. The membrane was incubated together with an anti-His-tag rabbit antibody. A molecule bound to the antibody was detected by the chemiluminescence method using an HRP-labeled anti-rabbit antibody. The results are shown in FIG. 2. In the Figure, lane 1 shows the result for mouse full-length FGF18 protein (the sequence depicted in SEQ ID NO:12 having the sequence depicted in SEQ ID NO:45 added thereto), and lanes 2 to 11 show the results for mouse mutant growth factor proteins (the sequences depicted in SEQ ID NO:13 to 22 each having the sequence depicted in SEQ ID NO:45 added thereto), and the lines at the left end of the lanes show the mobilities of the molecular weight marker for 37 KDa, 25 KDa, 20 KDa and 15 KDa, from top to bottom. It was confirmed that the individual proteins surely had the predicted molecular weights, and the proteins were collected.

The structures of the mouse full-length FGF18 protein (SEQ ID NO:12) and the mouse mutant FGF18 proteins (SEQ ID NOs:13 to 22), each expressed with a tag attached thereto, are shown schematically in FIG. 1.

(3) Heparin Affinity of Mutant FGF18 Proteins

Figure 3:
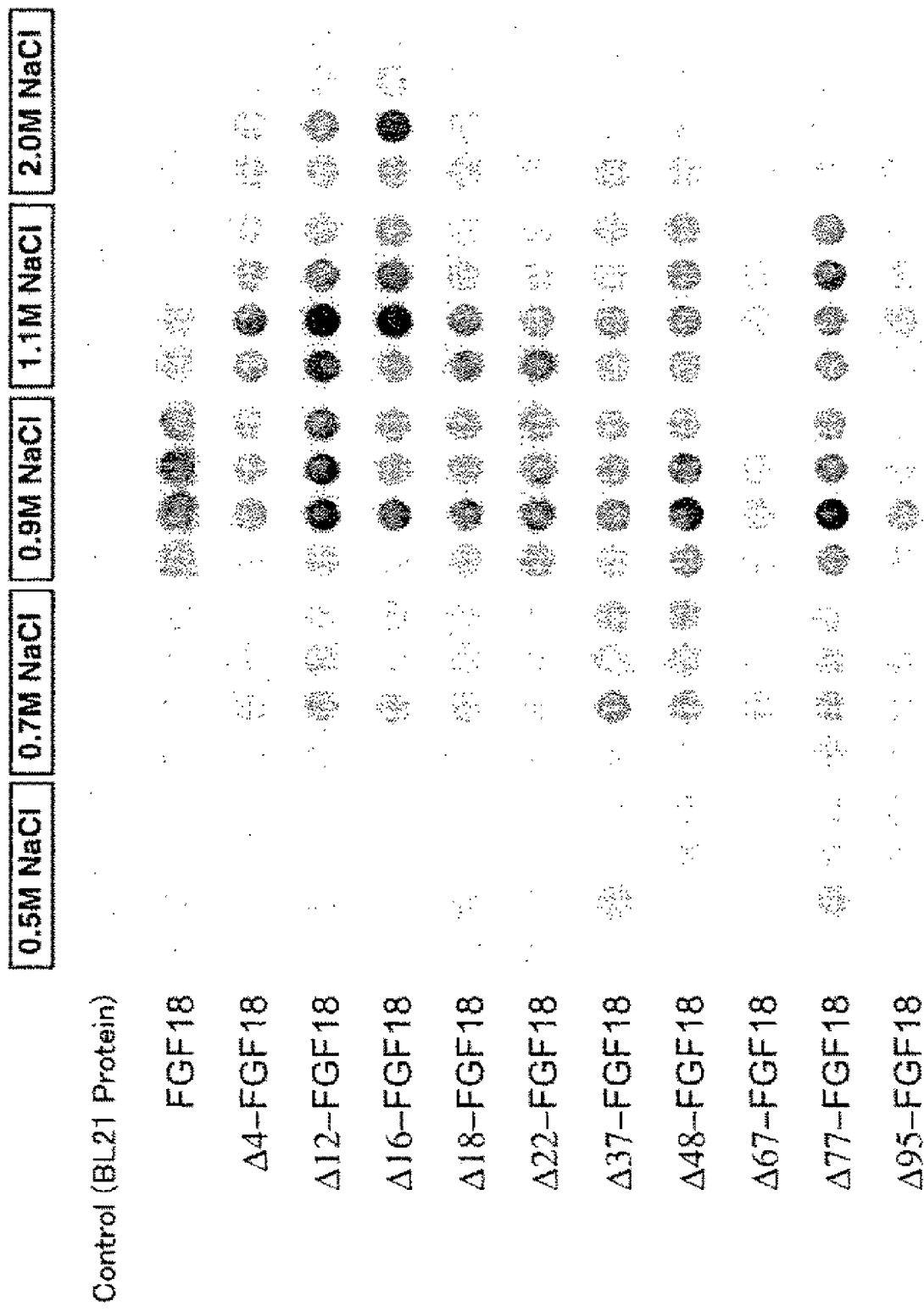
FIG. 3 shows the heparin affinity of mutant FGF18 proteins.

The mouse full-length FGF18 protein (SEQ ID NO:12) and the mutant mouse FGF18 proteins (SEQ ID NOs:13 to 22) were each expressed with a tag attached thereto, and adsorbed onto heparin sepharose beads. The beads were packed in a column, and washed with a phosphate buffered physiological saline. Subsequently, the column was washed with phosphate buffer solutions having successively increased NaCl concentrations. The wash solutions were collected and subjected to dot blotting. The results are shown in FIG. 3. In the Figure, the NaCl concentration is gradually increased from left to right. The mutant proteins contained in the eluates are detected with an antibody against the tag, and appear as black dot signals.

FIG. 3 demonstrates that the mouse full-length FGF18 protein has heparin affinity at approximately 0.9 M NaCl, that mutant Δ4- to Δ16-FGF18 proteins have heparin affinity at approximately 0.9 to 2.0 M NaCl, and that mutant Δ18- to Δ95-FGF18 proteins have heparin affinity at approximately 0.9 to 1.1 M NaCl.

(4) Growth Promotion Activity of Mutant FGF18 Proteins on FGFR4-Expressing Cell

Figure 4:
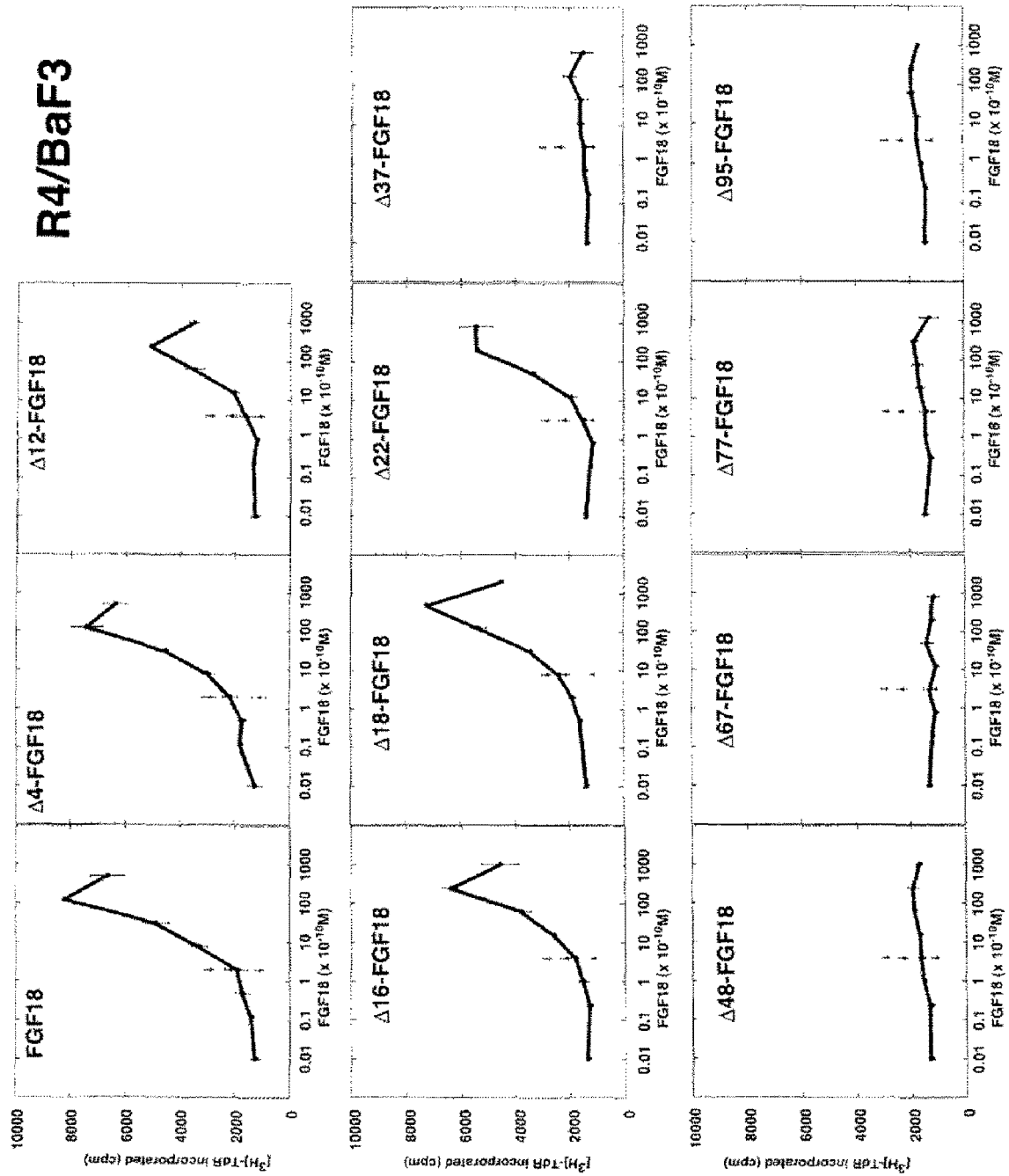
FIG. 4 shows the growth promotion activities of mutant FGF18 proteins on an FGFR4-expressing cell.

For an FGFR, an R4/BaF3 cell capable of expressing only FGFR4 was used [a BaF3 cell is available from Riken BRC; an R4/BaF3 cell was prepared by the present inventors (prepared in the same manner as disclosed in Yoneda A, Asada N, Oda Y, Suzuki M, Imamura T. (2000) Nature Biotechnology 18, 641-644, using a plasmid encoding an FGFR4 extracellular domain/FGFR1 intracellular domain chimera molecule (Ornitz D M, Xu J, Colvin J S, McEwen D G, MacArthur C A, Coulier F, Gao D, Goldfarb M (1996) J Biol Chem 271, 15292-15297))]. The R4/BaF3 cell was cultured in the presence of each of the mutant FGF18 proteins. The DNA synthesis (growth) of the cell was determined by measuring the 3H-thymidine uptake after a predetermined period of time. The results are shown in FIG. 4.

It is found that like the mouse full-length FGF18 protein, mutant Δ4- to Δ22-FGF18 proteins have a growth promotion activity on the R4/BaF3 cell; however, mutant Δ37- to Δ95-FGF18 proteins have little or no growth promotion activity on the R4/BaF3 cell.

Figure 5:
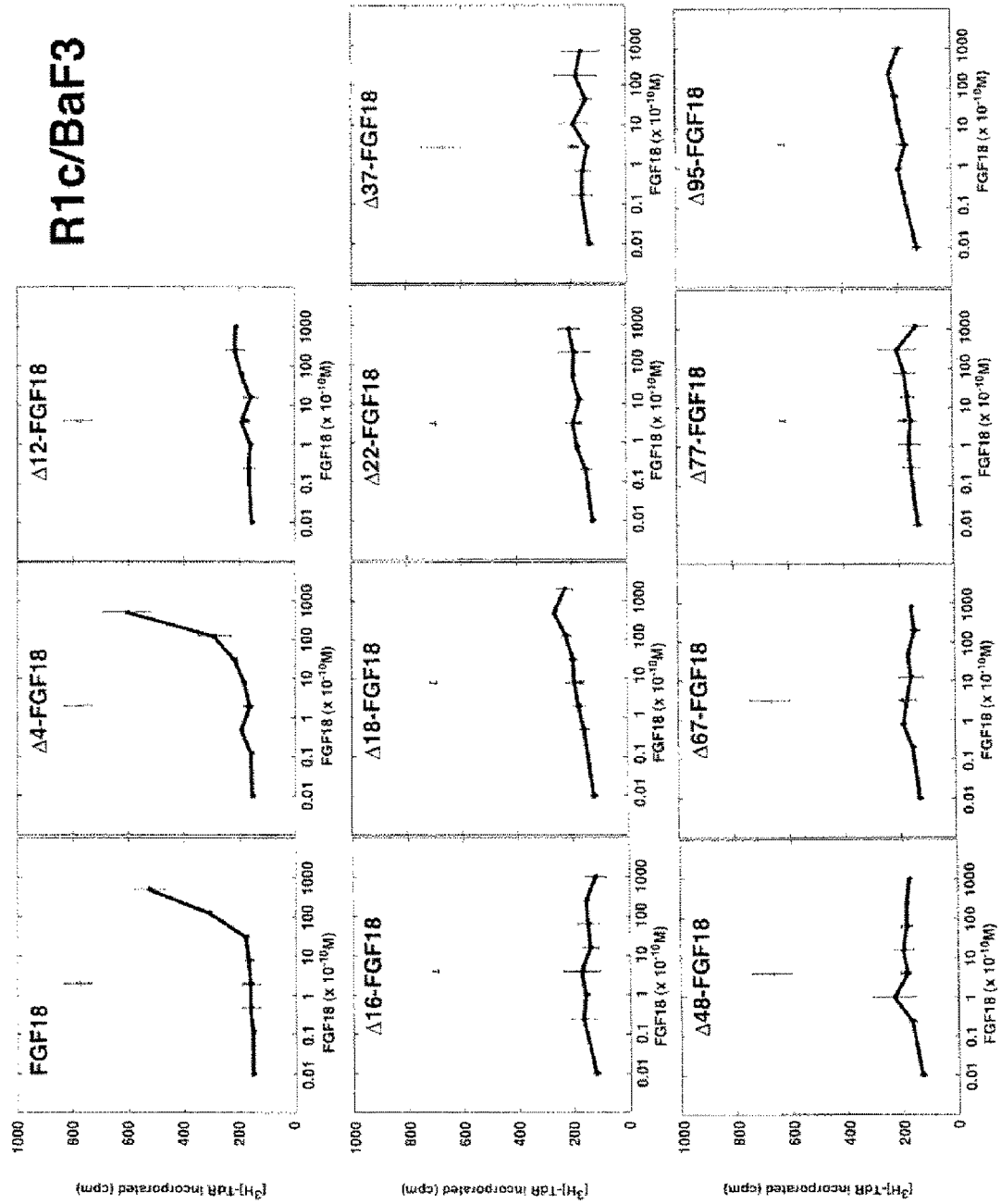
FIG. 5 shows the growth promotion activities of mutant FGF18 proteins on an FGFR1c-expressing cell.

(5) Growth Promotion Activity of Mutant FGF18 Proteins on FGFR1c-Expressing Cell For an FGFR, an R1c/BaF3 cell capable of expressing only FGFR1c was used [a BaF3 cell is available from Riken BRC; an R1c/BaF3 cell was prepared by the present inventors (prepared in the same manner as disclosed in Yoneda A, Asada M, Oda Y, Suzuki N, Imamura T. (2000) Nature Biotechnology 18, 641-644)]. The R1c/BaF3 cell was cultured in the presence of each of the mutant FGF18 proteins. The DNA synthesis (growth) of the cell was determined by measuring the 3H-thymidine uptake after a predetermined period of time. The results are shown in FIG. 5.

It is found that like the mouse full-length FGF18 protein, mutant Δ4-FGF18 protein has a growth promotion activity on the R1c/BaF3 cell; however, mutant Δ12- to Δ95-FGF18 proteins have little or no growth promotion activity on the R1c/BaF3 cell. Combining the results shown in FIGS. 4 and 5, one can see that mutant Δ12- to Δ22-FGF18 proteins react with FGFR4, but not with FGFR1c.

Figure 6:
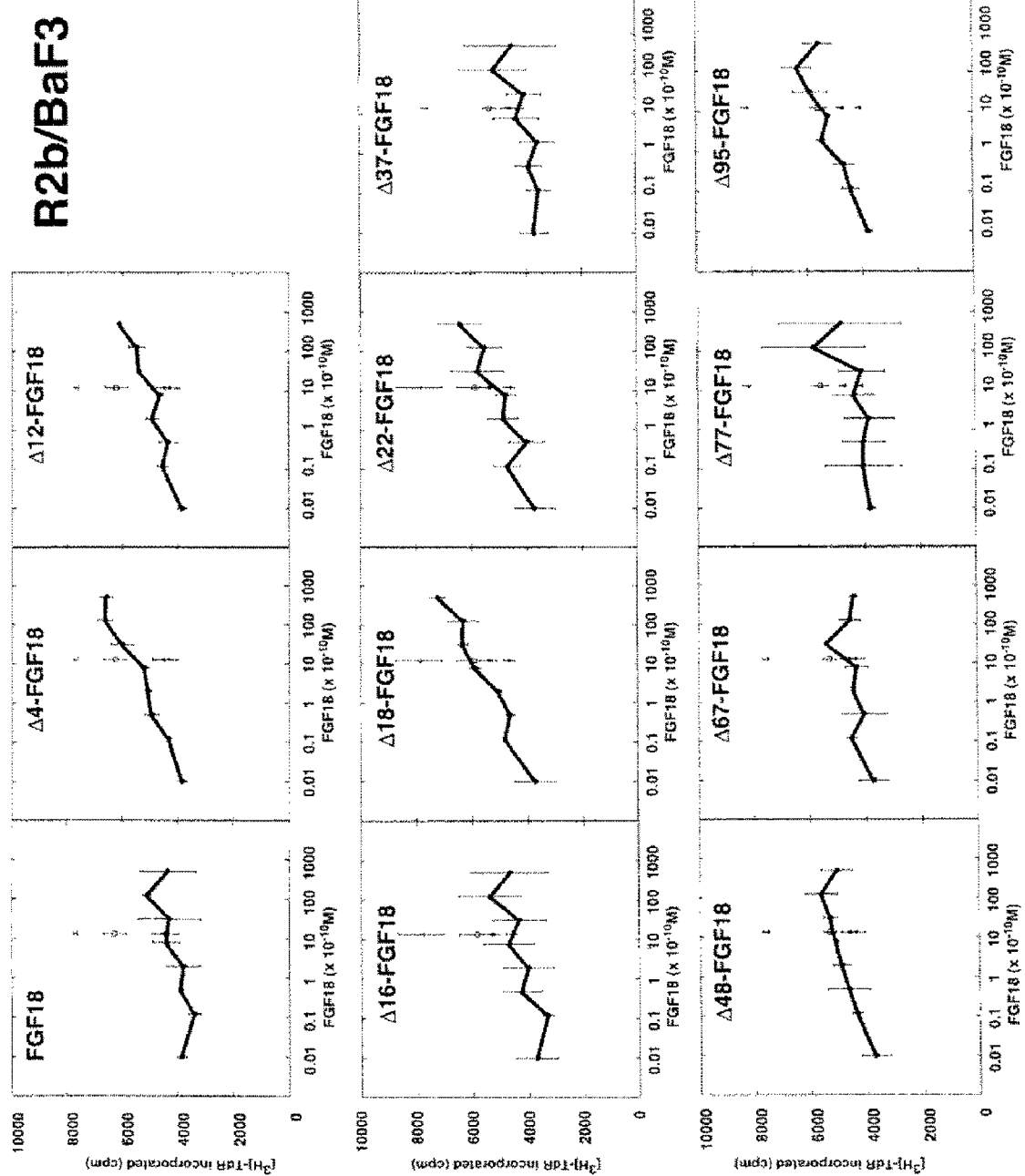
FIG. 6 shows the growth promotion activities of mutant FGF18 proteins on an FGFR2b-expressing cell.

(6) Growth Promotion Activity of Mutant FGF18 Proteins on FGFR2b-Expressing Cell For an FGFR, an R2b/BaF3 cell capable of expressing only FGFR2b was used [a BaF3 cell is available from Riken BRC; an R2b/BaF3 cell was prepared by the present inventors (prepared in the same manner as in the preparation of the R1c/BaF3 cell using a plasmid encoding an FGFR2b molecule (Ornitz D M, Xu J, Colvin J S, McEwen D G, MacArthur C A, Coulier F, Gao D, Goldfarb M (1996) J Biol Chem 271, 15292-15297))]. The R2b/BaF3 cell was cultured in the presence of each of the mutant FGF18 proteins. The DNA synthesis (growth) of the cell was determined by measuring the 3H-thymidine uptake after a predetermined period of time. The results are shown in FIG. 6.

Although it has not been reported previously that the mouse full-length FGF18 protein reacts with FGFR2b, these experimental results reveal that the mouse full-length FGF18 protein has a weak growth promotion activity on the R2b/BaF3 cell. It is also revealed that mutant Δ4- to Δ95-FGF18 proteins also have a weak growth promotion activity on the R2b/BaF3 cell.

Figure 7:
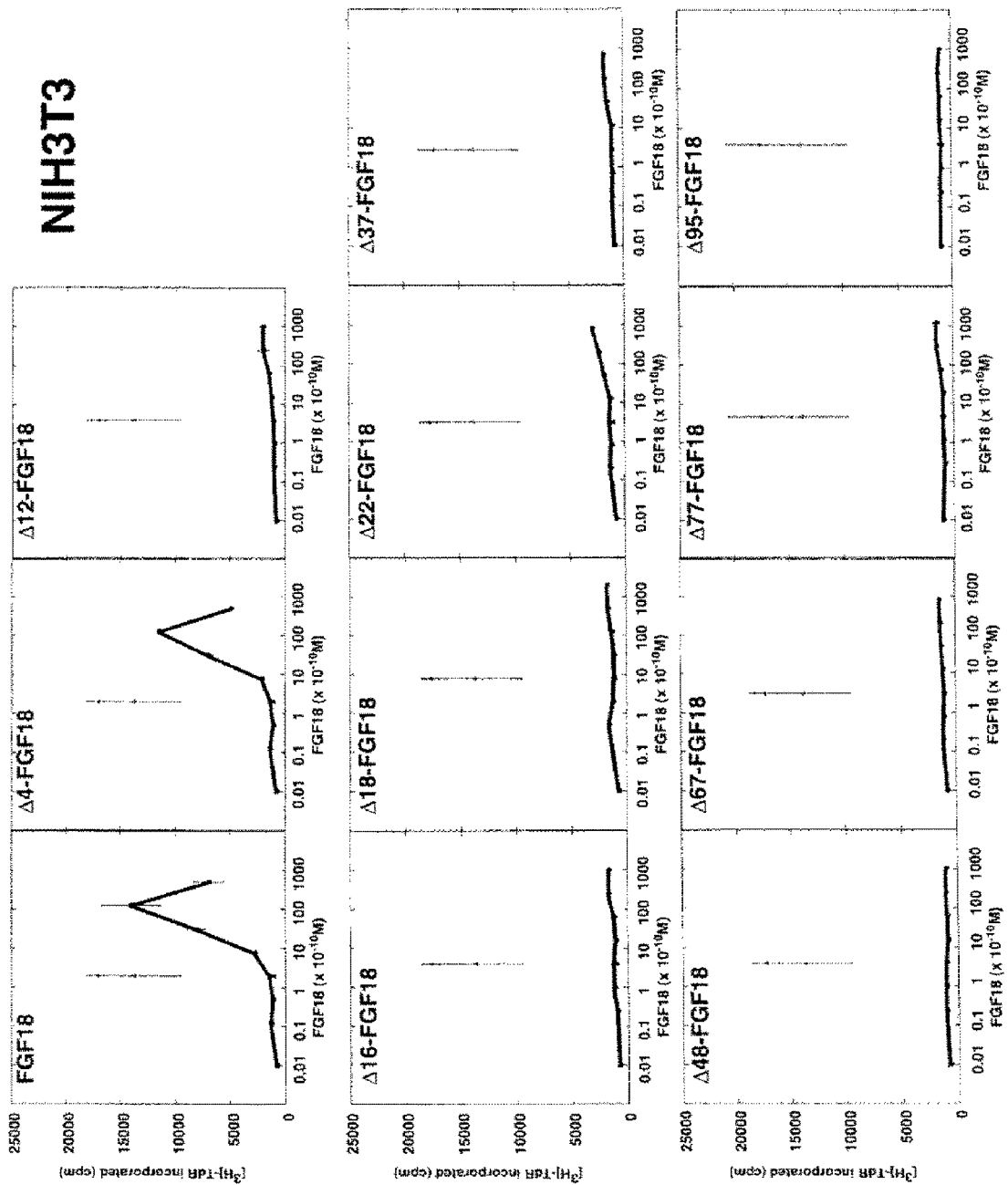
FIG. 7 shows the growth promotion activities of mutant FGF18 proteins on an NIH3T3 cell having an endogenous FGF receptor.

(7) Growth Promotion Activity of Mutant FGF18 Proteins on NIH3T3 Cell Having Endogenous FGF Receptor An NIH3T3 cell has an FGF receptor by nature, so it was examined whether mutant FGF18 proteins had a growth promotion activity on the cell. An NIH3T3 cell (available from ATCC) was serum-starved, and then cultured in the presence of each of the mutant FGF18 proteins. The DNA synthesis (growth) of the cell was determined by measuring the 3H-thymidine uptake after a predetermined period of time. The results are shown in FIG. 7.

It is found that both the mouse full-length FGF18 protein and mutant Δ4-FGF18 protein have a growth promotion activity on the NIH3T3 cell; mutant Δ12- to Δ37-FGF18 proteins have an extremely weak growth promotion activity on the NIH3T3 cell; and mutant Δ48- to Δ96-FGF18 proteins have no growth promotion activity on the NIH3T3 cell.

These results demonstrate that mutant Δ12- to Δ22-FGF18 proteins, which react with FGFR4 but not with FGFR1c, can be used to induce the FGFR4-mediated cellular reaction without inducing any action on the NIH3T3 cell.

In the above-mentioned experiments, the activities of mutant FGF18 proteins each having a tag attached thereto were determined. However, the tag was added after the C-terminus which is away from a region recognized as an FGF18 receptor-binding domain. Therefore, it is considered that the presence or absence of the tag has no influence on the binding between mutant FGF18 protein and its receptor. Further, although a heparin-binding domain is also located in close proximity to the receptor-binding domain in FGF18, the mutant FGF18 proteins each having a tag attached thereto that were used in the experiments keep high levels of binding affinity for heparin and therefore the activities of the mutant FGF18 proteins appear to be unaffected by the presence or absence of the tag.

The experimental data mentioned above are determined for mouse mutant FGF18 proteins. However, it is considered that the results on human mutant FGF18 proteins are approximately the same as those for mouse mutant FGF18 proteins. This is because the full-length FGF18 sequences of human and mouse (SEQ ID NOs:1 and 12) are identical with each other, except for one amino acid residue that is located at a position about 25 amino acid residues distant from the C-terminus and which has nothing to do with the locations where the deletions of amino acid residues occurred in the mutant FGF18 proteins prepared in the above experiments.

(8) Hair Growth/Nourishment Effect of Mutant FGF18 Proteins

This experiment used multiple seven-week-old C3H/HeN mice (male) which were in the telogen phase of the hair growth cycle. The hair of each mouse was shaved on its back, and 1 microgram of each of the mutant FGF18 proteins was injected to the mouse subcutaneously in the form of a physiological saline solution. The skin on the back of the mouse was observed for a period from week-3 to week-5, and the progress in the hair growth cycle of follicles was evaluated. When the skin darkened, it was determined that the anagen phase in the hair growth cycle had started. When the sprouting of a hair was observed, it was determined that the anagen phase further progressed.

(9) Bone Formation Activity of Mutant FGF18 Proteins

As a long bone epiphysis defect model, multiple 10-week-old ICR mice (male) were used in the animal experiment. Each mouse under anesthesia was drilled with a dental drill on the proximal end of the neck bone to form a circular bone hole having a diameter of 1 mm. The drill was pushed into the bone marrow through the bone hole to drill the cancellous bone, thereby forming a bone defect just before the opposite cortical bone. The defective area in the bone was filled with an FGF18 impregnated hydrogel. As a control, physiological saline was used. The cut area on the skin was closed. After recovery, the mice were raised without any constraint. The natural course of the mice was evaluated macroscopically, radiologically and histologically.

INDUSTRIAL APPLICABILITY

The mutant growth factor proteins of the present invention have different receptor specificities from the reaction specificity that naturally secreted FGF18 has for its receptor. The mutant growth factor proteins of the present invention can regulate a life process induced by naturally secreted FGF11.

[Sequence Listing Free Text]
<SEQ ID NO:1>
SEQ ID NO:1 represents an amino acid sequence of human full-length FGF18(-signal peptide).
<SEQ ID NO:2>
SEQ ID NO:2 represents an amino acid sequence of human Δ4-FGF18.
<SEQ ID NO:3>
SEQ ID NO:3 represents an amino acid sequence of human Δ12-FGF18.
<SEQ ID NO:4>
SEQ ID NO:4 represents an amino acid sequence of human Δ16-FGF18.
<SEQ ID NO:5>
SEQ ID NO:5 represents an amino acid sequence of human Δ18-FGF18.
<SEQ ID NO:6>
SEQ ID NO: 6 represents an amino acid sequence of human Δ22-FGF18.
<SEQ ID NO:7>
SEQ ID NO:7 represents an amino acid sequence of human Δ37-FGF18.
<SEQ ID NO:8>
SEQ ID NO:8 represents an amino acid sequence of human Δ48-FGF18.
<SEQ ID NO:9>
SEQ ID NO:9 represents an amino acid sequence of human Δ67-FGF18.
<SEQ ID NO:10>
SEQ ID NO:10 represents an amino acid sequence of human Δ77-FGF18.
<SEQ ID NO:11>
SEQ ID NO:11 represents an amino acid sequence of human Δ95-FGF18.
<SEQ ID NO:12>
SEQ ID NO: 12 represents an amino acid sequence of mouse full-length FGF18(-signal peptide).
<SEQ ID NO:13>
SEQ ID NO:13 represents an amino acid sequence of mouse Δ4-FGF18.
<SEQ ID NO:14>
SEQ ID NO:14 represents an amino acid sequence of mouse Δ12-FGF18.
<SEQ ID NO:15>
SEQ ID NO:15 represents an amino acid sequence of mouse Δ16-FGF18.
<SEQ ID NO:16>
SEQ ID NO:16 represents an amino acid sequence of mouse Δ18-FGF18.
<SEQ ID NO:17>
SEQ ID NO:17 represents an amino acid sequence of mouse Δ22-FGF18.
<SEQ ID NO:18>
SEQ ID NO:18 represents an amino acid sequence of mouse Δ37-FGF18.
<SEQ ID NO:19>
SEQ ID NO:19 represents an amino acid sequence of mouse Δ48-FGF18.
<SEQ ID NO:20>
SEQ ID NO: 20 represents an amino acid sequence of mouse Δ67-FGF18.
<SEQ ID NO:21>
SEQ ID NO: 21 represents an amino acid sequence of mouse Δ77-FGF18.
<SEQ ID NO:22>
SEQ ID NO: 22 represents an amino acid sequence of mouse Δ95-FGF18.

<SEQ ID NO:23>
SEQ ID NO:23 represents a DNA sequence encoding human full-length FGF18(-signal peptide).
<SEQ ID NO:24>
SEQ ID NO:24 represents a DNA sequence encoding human Δ4-FGF18.
<SEQ ID NO:25>
SEQ ID NO:25 represents a DNA sequence encoding human Δ12-FGF18.
<SEQ ID NO:26>
SEQ ID NO:26 represents a DNA sequence encoding human Δ16-FGF18.
<SEQ ID NO:27>
SEQ ID NO:27 represents a DNA sequence encoding human Δ18-FGF18.
<SEQ ID NO:28>
SEQ ID NO:28 represents a DNA sequence encoding human Δ22-FGF18.
<SEQ ID NO:29>
SEQ ID NO:29 represents a DNA sequence encoding human Δ37-FGF18.
<SEQ ID NO:30>
SEQ ID NO:30 represents a DNA sequence encoding human Δ48-FGF18.
<SEQ ID NO:31>
SEQ ID NO:31 represents a DNA sequence encoding human Δ67-FGF18.
<SEQ ID NO:32>
SEQ ID NO:32 represents a DNA sequence encoding human Δ77-FGF18.
<SEQ ID NO:33>
SEQ ID NO:33 represents a DNA sequence encoding human Δ95-FGF18.
<SEQ ID NO:34>
SEQ ID NO: 34 represents a DNA sequence encoding mouse full-length FGF18(-signal peptide).
<SEQ ID NO:35>
SEQ ID NO:35 represents a DNA sequence encoding mouse Δ4-FGF18.
<SEQ ID NO:36>
SEQ ID NO:36 represents a DNA sequence encoding mouse Δ12-FGF18.
<SEQ ID NO:37>
SEQ ID NO:37 represents a DNA sequence encoding mouse Δ16-FGF18.
<SEQ ID NO:38>
SEQ ID NO:38 represents a DNA sequence encoding mouse Δ18-FGF18.
<SEQ ID NO:39>
SEQ ID NO:39 represents a DNA sequence encoding mouse Δ22-FGF18.
<SEQ ID NO:40>
SEQ ID NO:40 represents a DNA sequence encoding mouse Δ37-FGF18.
<SEQ ID NO:41>
SEQ ID NO:41 represents a DNA sequence encoding mouse Δ48-FGF1.
<SEQ ID NO:42>
SEQ ID NO:42 represents a DNA sequence encoding mouse Δ67-FGF18.
<SEQ ID NO:43>
SEQ ID NO:43 represents a DNA sequence encoding mouse Δ77-FGF18.
<SEQ ID NO:44>
SEQ ID NO:44 represents a DNA sequence encoding mouse Δ95-FGF18.
<SEQ ID NO:45>
SEQ ID NO: 45 represents an amino acid sequence of a FLAG-His tag tag.
<SEQ ID NO:46>
SEQ ID NO:46 represents a DNA sequence of a FLAG-His tag.
<SEQ ID NO:47>
SEQ ID NO: 47 represents an amino acid sequence of a signal peptide for human FGF18.
<SEQ ID NO:48>
SEQ ID NO:48 represents a DNA sequence of a signal peptide for human FGF18.
<SEQ ID NO:49>
SEQ ID NO: 49 represents an amino acid sequence of a signal peptide for mouse FGF18.
<SEQ ID NO:50>
SEQ ID NO:50 represents a DNA sequence of a signal peptide for mouse FGF18.
<SEQ ID NO:51>
SEQ ID NO: 51 represents a DNA sequence of a primer (a sense primer) for use in the amplification of cDNA encoding mouse full-length
FGF18 (full-length including a signal sequence).
<SEQ ID NO:52>
SEQ ID NO:52 represents a DNA sequence of a primer (an antisense primer) for use in the amplification of cDNA encoding mouse full-length FGF18 (full-length including a signal sequence).
<SEQ ID NO:53>
SEQ ID NO:53 represents a DNA sequence of a primer #468.
<SEQ ID NO:54>
SEQ ID NO:54 represents a DNA sequence of a primer #469.
<SEQ ID NO:55>
SEQ ID NO:55 represents a DNA sequence of a primer #466.
<SEQ ID NO:56>
SEQ ID NO:56 represents a DNA sequence of a primer #467.
<SEQ ID NO:57>
SEQ ID NO:57 represents a DNA sequence of a primer (a sense primer) for use in the amplification of cDNA encoding mouse full-length FGF18 (without a signal sequence),
<SEQ ID NO:58>
SEQ ID NO:58 represents a DNA sequence of a primer #226.
<SEQ ID NO:59>
SEQ ID NO:59 represents a DNA sequence of a primer #249.
<SEQ ID NO:60>
SEQ ID NO:60 represents a DNA sequence of a primer #262.
<SEQ ID NO:61>
SEQ ID NO:61 represents a DNA sequence of a primer #268.
<SEQ ID NO:62>
SEQ ID NO:62 represents a DNA sequence of a primer #280.
<SEQ ID NO:63>
SEQ ID NO:63 represents a DNA sequence of a primer #325.
<SEQ ID NO:64>
SEQ ID NO:64 represents a DNA sequence of a primer #358.
<SEQ ID NO:65>
SEQ ID NO:65 represents a DNA sequence of a primer #415.
<SEQ ID NO:66>
SEQ ID NO:66 represents a DNA sequence of a primer #445.
<SEQ ID NO:67>
SEQ ID NO:67 represents a DNA sequence of a primer #498.
<SEQ ID NO:68>
SEQ ID NO:68 represents a DNA sequence of a primer #537 (an antisense primer) for use in the amplification of cDNA having mouse full-length FGF18 (without a signal sequence).

<SEQ ID NO:69>
SEQ ID NO: 69 represents a DNA sequence of a primer (a sense primer) for use in the amplification of cDNA encoding human full-length FGF18 (full-length including a signal sequence).
<SEQ ID NO:70>
SEQ ID NO:70 represents a DNA sequence of a primer (antisense primer) for use in the amplification of cDNA encoding human full-length FGF18 (full-length including a signal sequence).
<SEQ ID NO:71>
SEQ ID NO:71 represents a DNA sequence of a primer (which can be used in place of a primer #325) for use in the amplification of cDNA encoding a protein comprising a human mutant FGF18 having a FLAG-His tag attached at the C-terminus thereof.

What is claimed is:

1. An isolated protein comprising:
a mutant protein of a naturally secreted fibroblast growth factor 18, which has 12 to 22 amino acid residues deleted from the N-terminus of the amino acid sequence of the naturally secreted fibroblast growth factor 18 such that the mutant protein binds to FGFR4 but fails to bind to FGFR1c and/or to stimulate NIH3T3 cell proliferation.

2. The isolated protein according to claim 1, wherein the mutant protein comprises the amino acid sequence of any one of SEQ ID NOs:2 to 11 or 13 to 22.

3. A pharmaceutical composition comprising a protein as recited in claims 1 or 2.

4. The pharmaceutical composition according to claim 3 formulated to bind to fibroblast growth factor receptor 4 to regulate a cellular function, wherein the pharmaceutical composition is a liquid, a lotion, an aerosol, an injection, a powder, a granule, a tablet, a suppository, an enteric coated tablet or a capsule.

5. The pharmaceutical composition according to claim 3 formulated to regulate hair regeneration or hair growth, wherein the pharmaceutical composition is a liquid, a lotion, an aerosol, an injection, a powder, a granule, a tablet, a suppository, an enteric coated tablet or a capsule.

6. The pharmaceutical composition according to claim 3 formulated to regulate bone or cartilage formation, wherein the pharmaceutical composition is a liquid, a lotion, an aerosol, an injection, a powder, a granule, a tablet, a suppository, an enteric coated tablet or a capsule.

7. The mutant protein according to claim 1, further comprising a secreted signal sequence and/or a tag sequence.

8. An isolated protein comprising:
a mutant protein of a naturally secreted fibroblast growth factor 18, which has 4 to 22 amino acid residues other than methionine deleted from the N-terminus of the amino acid sequence of naturally the secreted fibroblast growth factor 18.

9. A pharmaceutical composition comprising a protein as recited in claim 8.

10. The pharmaceutical composition according to claim 9 formulated to bind to fibroblast growth factor receptor 4 to regulate a cellular function, wherein the pharmaceutical composition is a liquid, a lotion, an aerosol, an injection, a powder, a granule, a tablet, a suppository, an enteric coated tablet or a capsule.

11. The pharmaceutical composition according to claim 9 formulated to regulate hair regeneration or hair growth, wherein the pharmaceutical composition is a liquid, a lotion, an aerosol, an injection, a powder, a granule, a tablet, a suppository, an enteric coated tablet or a capsule.

12. The pharmaceutical composition according to claim 9 formulated to regulate bone or cartilage formation, wherein the pharmaceutical composition is a liquid, a lotion, an aerosol, an injection, a powder, a granule, a tablet, a suppository, an enteric coated tablet or a capsule.

13. A method for producing a mutant protein having an altered fibroblast growth factor receptor specificity, which comprises deleting 12 to 22 amino acid residues from the N-terminus of the amino acid sequence of naturally secreted fibroblast growth factor 18, whereby the mutant protein binds to FGFR4 but fails to bind to FGFR1c and/or to stimulate NIH3T3 cell proliferation.

* * * * *